US008896835B2

(12) United States Patent
Ido et al.

(10) Patent No.: US 8,896,835 B2
(45) Date of Patent: Nov. 25, 2014

(54) GAS MEASUREMENT APPARATUS AND THE SETTING METHOD OF WIDTH OF WAVELENGTH MODULATION IN GAS MEASUREMENT APPARATUS

(71) Applicant: Horiba, Ltd., Kyoto (JP)

(72) Inventors: Takuya Ido, Kyoto (JP); Tetsuya Mori, Kyoto (JP)

(73) Assignee: Horiba, Ltd., Kyoto (JP)

( * ) Notice: Subject to any disclaimer, the term of this patent is extended or adjusted under 35 U.S.C. 154(b) by 151 days.

(21) Appl. No.: 13/723,367

(22) Filed: Dec. 21, 2012

(65) Prior Publication Data

US 2013/0163000 A1 Jun. 27, 2013

(30) Foreign Application Priority Data

Dec. 27, 2011 (JP) ................................ 2011-286765
Dec. 27, 2011 (JP) ................................ 2011-286895

(51) Int. Cl.
*G01N 21/00* (2006.01)
*G01B 11/14* (2006.01)
*G01N 21/35* (2014.01)
*G01J 3/433* (2006.01)
*G01N 21/59* (2006.01)

(52) U.S. Cl.
CPC ................ *G01N 21/59* (2013.01); *G01B 11/14* (2013.01); *G01N 21/3504* (2013.01); *G01J 3/4338* (2013.01)
USPC ........... 356/437; 356/432; 356/442; 356/614; 356/617

(58) Field of Classification Search
USPC .................................................... 356/432–44
See application file for complete search history.

(56) References Cited

U.S. PATENT DOCUMENTS 5,002,391 A * 3/1991 Wolfrum et al. .............. 356/307
5,317,156 A * 5/1994 Cooper et al. ................ 250/345
6,044,329 A 3/2000 Kidd
6,351,309 B1 2/2002 Bomse et al.

(Continued)

FOREIGN PATENT DOCUMENTS

JP 63-182550 A 7/1988
JP 04326041 11/1992

(Continued)

OTHER PUBLICATIONS

Extended European Search Report, Application No. 12008570.9-1554 dated May 17, 2013.

*Primary Examiner* — Tarifur Chowdhury
*Assistant Examiner* — Jarreas C Underwood
(74) *Attorney, Agent, or Firm* — Brooks Kushman P.C.

(57) ABSTRACT

A gas measurement apparatus measures a target gas. The gas measurement apparatus includes a light source, a first light receiving apparatus, a first phase-sensitive detection apparatus, an R calculation unit, and a setting unit. The light source oscillates a laser light that has a central wavelength determined by a main current and is modulated according to a modulation current, with the central wavelength being varied. The first light receiving apparatus outputs a detection signal according to an intensity of the laser light transmitted through a standard sample. The first phase-sensitive detection apparatus obtains a second harmonic component oscillated at a harmonic frequency ω2 twice as large as a modulation frequency ω1. The R calculation unit calculates a peak-bottom ratio R. The setting unit sets a width of wavelength modulation of the laser light so that the peak-bottom ratio R satisfies a predetermined condition.

20 Claims, 17 Drawing Sheets

100
Start
Sweep start S101
Obtain detection signal S102
S103 Obtain harmonic component
Sweep end? S104 N Y
Calculate R S105
Does R agree with target value? S106 N Y
S107 Change modulation current
End

(56) References Cited

U.S. PATENT DOCUMENTS

| | | | | |
|---|---|---|---|---|
| 6,519,039 | B1 * | 2/2003 | Morishita et al. | 356/437 |
| 2006/0187976 | A1 * | 8/2006 | Mori et al. | 372/20 |
| 2009/0164138 | A1 | 6/2009 | Goto et al. | |
| 2011/0181879 | A1 | 7/2011 | Chen et al. | |
| 2013/0321815 | A1 * | 12/2013 | Otera | 356/437 |

FOREIGN PATENT DOCUMENTS

| | | |
|---|---|---|
| JP | 2703835 | 1/1998 |
| JP | 2001074654 | 3/2001 |
| JP | 2008147557 | 6/2008 |
| JP | 4199766 | 12/2008 |
| JP | 4467674 | 5/2010 |

* cited by examiner

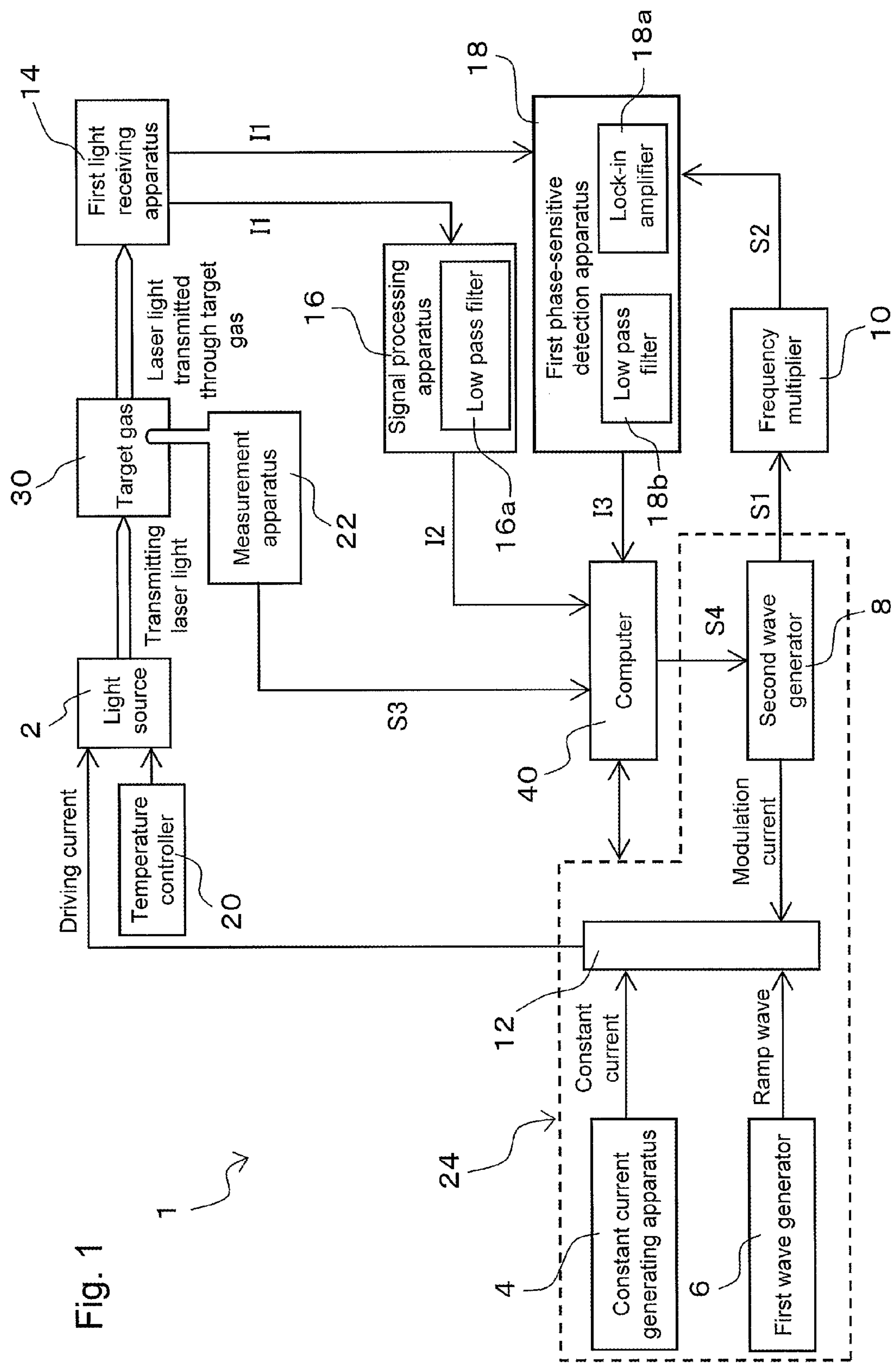
Fig. 1
1
First light receiving apparatus
14
Laser light transmitted through target gas
Target gas
30
Transmitting laser light
Light source
2
Temperature controller
20
Driving current
Measurement apparatus
22
Signal processing apparatus
Low pass filter
16
16a
I1
I1
I2
First phase-sensitive detection apparatus
Lock-in amplifier
Low pass filter
18
18a
18b
I3
S2
Frequency multiplier
10
S1
Computer
40
S3
S4
Second wave generator
8
Modulation current
12
Constant current
Ramp wave
24
Constant current generating apparatus
4
First wave generator
6

Base line
AP
AN
P
N

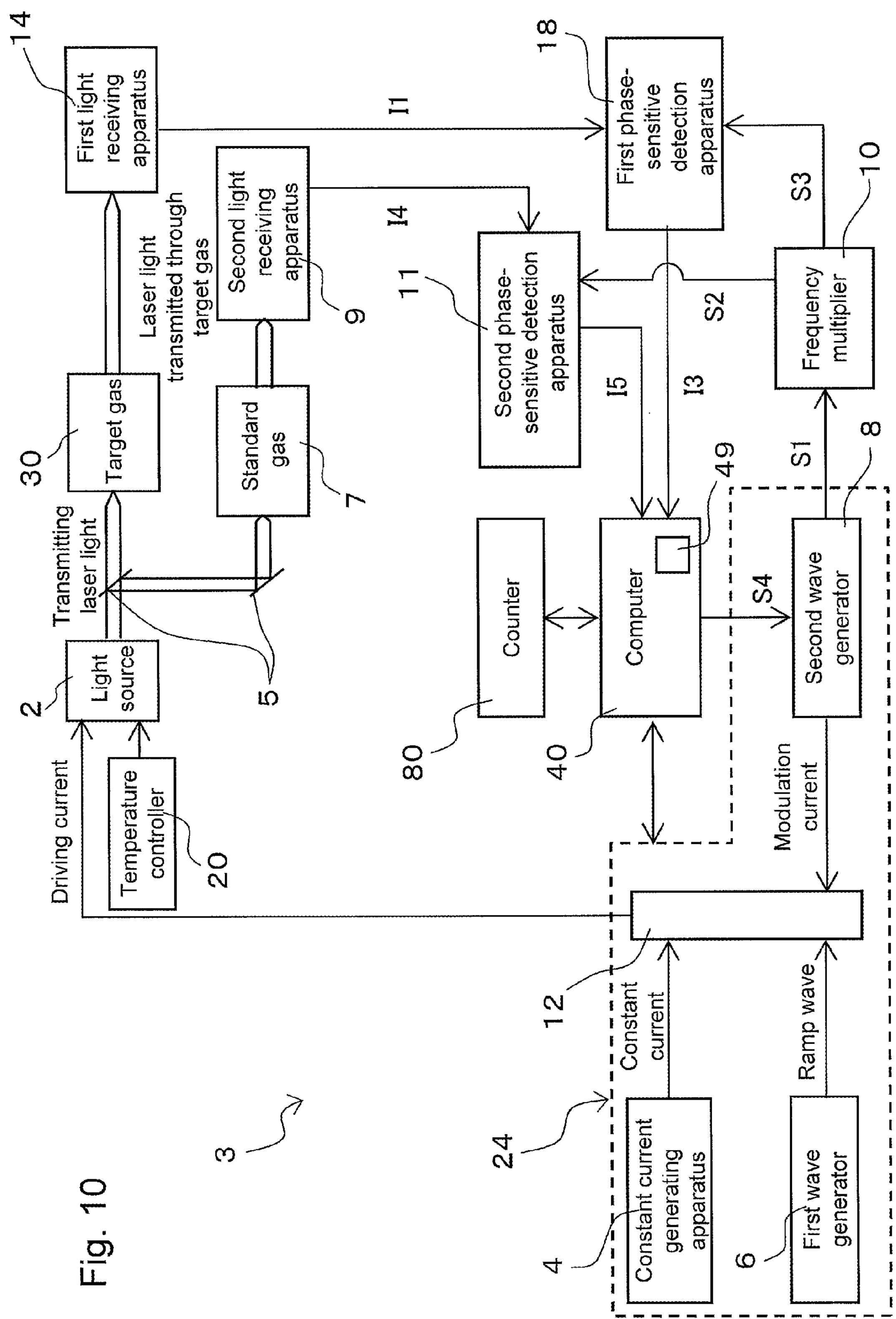

Fig. 10
3
14
First light receiving apparatus
I1
18
First phase-sensitive detection apparatus
Second light receiving apparatus
9
I4
11
Second phase-sensitive detection apparatus
S2
Frequency multiplier
10
S3
Laser light transmitted through target gas
30
Target gas
Standard gas
7
I5
I3
S1
8
49
Transmitting laser light
2
Light source
5
Counter
80
Computer
40
S4
Second wave generator
Driving current
Temperature controller
20
Modulation current
12
Constant current
Ramp wave
24
4
Constant current generating apparatus
6
First wave generator (B)

Fig. 16

| Q \ T | $T_1$ | $T_2$ | $T_3$ | $T_4$ | … |
|---|---|---|---|---|---|
| $Q_1$ | $R_{11}$ | $R_{12}$ | $R_{13}$ | $R_{14}$ | … |
| $Q_2$ | $R_{21}$ | $R_{22}$ | $R_{23}$ | $R_{24}$ | … |
| $Q_3$ | $R_{31}$ | $R_{32}$ | $R_{33}$ | $R_{34}$ | … |
| $Q_4$ | $R_{41}$ | $R_{42}$ | $R_{43}$ | $R_{44}$ | … |
| … | … | … | … | … | ⋰ |

GAS MEASUREMENT APPARATUS AND THE SETTING METHOD OF WIDTH OF WAVELENGTH MODULATION IN GAS MEASUREMENT APPARATUS

CROSS-REFERENCE TO RELATED APPLICATIONS

This application claims priority under 35 U.S.C. §119 to Japanese Patent Applications No. 2011-286765 and No. 2011-286895 filed on Dec. 27, 2011. The entire disclosure of Japanese Patent Applications No. 2011-286765 and No. 2011-286895 is hereby incorporated herein by reference.

BACKGROUND

1. Field of the Invention

The present invention relates to a gas measurement apparatus using Tunable Laser Absorption Spectroscopy (TLAS) and Wavelength Modulation Spectroscopy (WMS) and a method of setting a width of wavelength modulation in the gas measurement apparatus.

2. Description of the Related Art

Conventionally, a gas measurement apparatus using TLAS has been known. A laser used in TLAS oscillates a laser light whose intensity is determined by a driving current of the laser and temperatures. The gas measurement apparatus using TLAS measures parameters of a target gas by transmitting the laser light through the target gas and detecting the laser light transmitted through the target gas. For example, a concentration of a target component included in a gas can be measured. A ratio of an intensity of a laser light transmitted through a target gas relative to a laser light oscillated from a laser is defined as a transmittance T. T is expressed as $T=e^{-\epsilon cl}$, where $\epsilon$ is a molar absorption coefficient, c is a concentration of a target component, and l is an optical path length. It is also known that a molar absorption coefficient $\epsilon$ depends on a temperature of a target gas, and that a shape of an absorption line depends on temperatures, pressures, and partial pressures of components coexisted in a target gas. A concentration of a target component can be determined by measuring a transmittance T if an optical path length l is known and it is known how a molar absorption coefficient $\epsilon$ and a shape of an absorption line depend on temperatures, pressures, and partial pressures of components coexisted in a target gas.

A wavelength modulation spectroscopy (WMS) can be used for measuring gas parameters using TLAS. In WMS, a laser light with modulated wavelength and/or intensity is oscillated by varying a driving current or a temperature of the laser. Then, the modulated laser light transmits through a target gas and the transmitted laser light is detected. A detection signal is then generated in accordance with the detected laser light. Further, a specific component of the detection signal is obtained by performing a phase-sensitive detection to the detection signal and a concentration of a target component is measured by using the detected specific component (For example, refer to Japanese Patent 2703835 and Japanese Patent 4467674).

In using WMS, an extent of a wavelength modulation can be expressed as a width of wavelength modulation. For an accurate measurement of gas parameters, this width needs to be appropriately set. The main reason for this is that a width of wavelength modulation is a factor that determines a resolution and a signal to noise ratio (expressed as a S/N ratio hereinafter) of an apparatus. A width of wavelength modulation is determined by an intensity of a modulation current included in the driving current. Therefore, the intensity of the modulation current needs to be set in order to set the width of wavelength modulation. Here, a variation rate of the wavelength to the driving current, namely a ratio of the variation of the wavelength of the laser light relative to the variation of the intensity of the driving current, is different between laser devices. Namely, since the intensity of an optimal modulation current is different between apparatuses, a setting of the modulation current needs to be performed in each apparatus. In general, the variation rate of the wavelength relative to the driving current changes over time by operating a laser. Therefore, in order for each apparatus to keep the width of wavelength modulation in an appropriate value, the modulation current needs to be adjusted in accordance with the operation of the apparatus.

A use of a wavelength measurement apparatus and a gas that has a known absorption line can be considered as means for setting a intensity of a modulation current. In using these means, a ratio of the variation of the wavelength of the laser light relative to the variation of the driving current is measured by measuring the wavelength of the laser light. Then, based on the measured ratio, the intensity of the modulation current is set to obtain a desired width of wavelength modulation. However, in using the above means, the following may be problems: (1) the gas appropriate for the wavelength measurement apparatus or the wavelength measurement needs to be prepared. In addition, the gas measurement apparatus and the wavelength measurement apparatus need to be moved in the case where the gas measurement apparatus has already been installed in the place where a target gas exists, because the gas measurement apparatus and the wavelength apparatus need to be installed to perform the wavelength measurement; and (2) a work efficiency is lowered and a time and an effort for setting the modulation current increases because the wavelength of the laser light needs to be measured.

SUMMARY

The present invention was conceived in light of the above-described problem, and is generally directed to simplifying setting of a width of wavelength modulation in a gas measurement apparatus.

A gas measurement apparatus according to a first aspect of the present invention measures a target gas. The gas measurement apparatus comprises a light source, a detection unit, an obtaining unit, a calculation unit, and a setting unit. The light source oscillates a laser light that has a central wavelength determined by a main current and is modulated according to a modulation current, with the central wavelength being varied. The detection unit outputs a detection signal according to an intensity of the laser light transmitted through a standard sample. The obtaining unit obtains a specific frequency component of the detection signal that is oscillated at a frequency that is a positive integral multiple of an oscillation frequency of the modulation current. The calculation unit calculates a ratio of a magnitude of a local minimum of the specific frequency component and a magnitude of a local maximum of the specific frequency component. The setting unit sets a width of wavelength modulation of the laser light so that the ratio satisfies a predetermined condition.

A method according to a second aspect of the present invention is a method of setting a width of wavelength modulation of a gas measurement apparatus. The gas measurement apparatus comprises a light source configured to oscillate an laser light that has a central wavelength determined by a main current and is modulated according to a modulation current, and a detection unit configured to output a signal according to an intensity of the laser light transmitted through a target gas.

The method comprises a step of obtaining a detection signal by detecting the laser light transmitted through the standard sample, with the central wavelength being varied. This method also comprises a step of obtaining a specific frequency component of the detection signal that is oscillated at a frequency that is a positive integral multiple of an oscillation frequency of the modulation current. This method also comprises a step of calculating a ratio of a magnitude of a local minimum of the specific frequency component and a magnitude of a local maximum of the specific frequency component. Then, this method comprises setting the width of wavelength modulation of the laser light so that the ratio satisfies a predetermined condition.

A storage medium according to a third aspect of the present invention stores a program that causes a computer to perform a method of setting a width of wavelength modulation used by a gas measurement apparatus. The gas measurement apparatus comprises a light source, a detection unit, and an obtaining unit. The light source oscillates a laser light that has a central wavelength determined by a main current and is modulated according to a modulation current with the central wavelength being varied. The detection unit outputs a detection signal according to an intensity of the laser light transmitted through a standard sample. The obtaining unit obtains a specific frequency component of the detection signal that is oscillated at a frequency that is a positive integral multiple of an oscillation frequency of the modulation current. The method comprises a step of calculating a ratio of a magnitude of a local minimum of the specific frequency component and a magnitude of local maximum of the specific frequency component, and a step of setting a width of wavelength modulation of the laser light so that the ratio meets a predetermined condition.

These and other objects, features, aspects and advantages of the present invention will become apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure:

FIG. 1 is a schematic diagram of a gas measurement apparatus 1 according to a first embodiment.

FIG. 10 is a schematic diagram of a gas measurement apparatus according to a third embodiment.

FIG. 16 is a graph that shows a predetermined relationship between a temperature, a pressure, and a peak-bottom ratio R.

DETAILED DESCRIPTION

Figure 2:
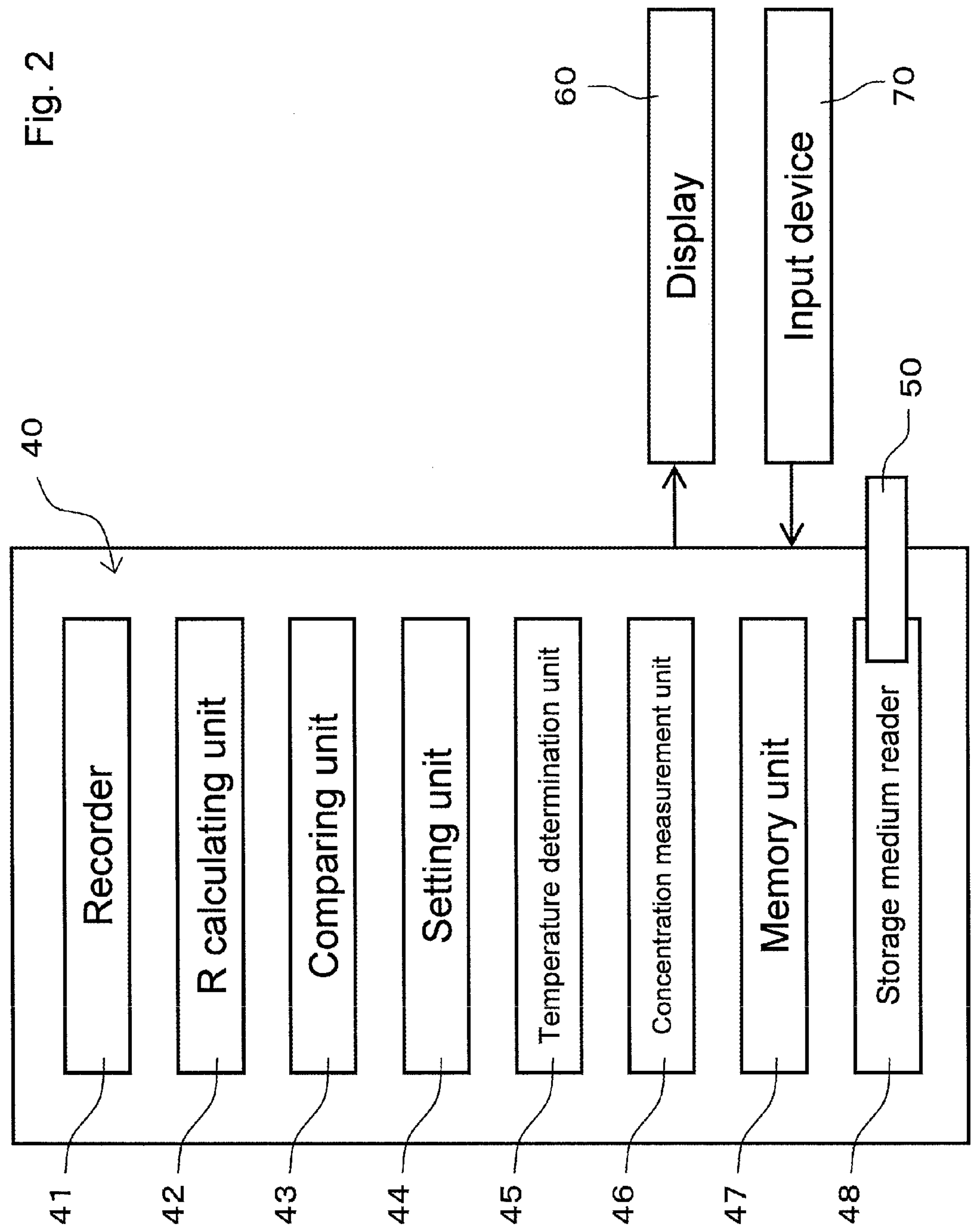
FIG. 2 is a block diagram that shows functioning units of a computer 40.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Selected embodiments of the present invention will now be explained with reference to the drawings. It will be apparent to those skilled in the art from this disclosure that the following descriptions of the embodiments of the present invention are provided as examples only and are not meant to limit the invention defined by the appended claims and their equivalents.

1. First Embodiment 1.1 Overall Structure

Hereinafter, one embodiment according to the present invention will be explained with the accompanying drawings. FIG. 1 is a schematic of a gas measurement apparatus 1 according to a first embodiment.

A gas measurement apparatus 1 comprises a light source 2, a frequency multiplier 10, a first light receiving apparatus 14, a signal processing apparatus 16, a first phase-sensitive detection apparatus 18, a temperature controller 20, a measurement apparatus 22, a wave generating unit 24, and a computer 40. The wave generating unit 24 includes a constant current generating apparatus 4, a first wave generator 6, a second wave generator 8, and a wave mixer 12.

The light source 2 is an apparatus that oscillates a laser light with a wavelength and an intensity determined in accordance with a driving current. The light source 2 is typically a semiconductor laser.

It should be noted that the driving current inputted to the light source 2 includes a main current and a modulation current. The modulation current is a current oscillated at a modulation frequency ω1 (an example of a modulation current). The modulation current has constant amplitude. A magnitude of the amplitude of the modulation current represents an intensity of the modulation current. The main current is a current with an intensity varied in a longer cycle than that of the modulation current. This means that the intensity of the main current can be considered almost constant during one cycle of the oscillation of the modulation current. In this case, the main current determines a central wavelength of the laser light oscillated by the light source 2. The wavelength of the laser light oscillated by the light source 2 is then modulated in accordance with the modulation current (wavelength modulation). Thus, the light source 2 can oscillate a laser light that is wavelength-modulated with the central wavelength, with the central wavelength of the laser light being varied. It is also noted that the main current can be generated by convoluting a constant current and a ramp current. The constant current is a current with a constant intensity. The ramp current is a current that iterates oblique increases and reversions to a base level periodically.

The constant current generating apparatus 4 generates the constant current inputted to the light source 2. The first wave generator 6 generates the ramp current inputted to the light source 2.

The second wave generator 8 generates the modulation current inputted to the light source 2. The second wave generator 8 also outputs a modulation signal S1 oscillated at the modulation frequency ω1. It should be noted that the modulation frequency ω1 is larger than a frequency of the ramp current. Further, the second wave generator 8 receives a control signal S4. The frequency multiplier 10 generates a signal S2 oscillated at a harmonic frequency ω2 that is twice as large as the modulation frequency ω1, based on the modulation signal S1 outputted from the second wave generator 8. The wave mixer 12 generates the driving current by mixing the constant current outputted from the constant current generating apparatus 4, the ramp current outputted from the first wave generator 6, and the modulation current outputted from the second wave generator 8.

The first light receiving apparatus 14 (an example of a detection unit) receives the laser light oscillated by the light source 2. The first light receiving apparatus 14 also outputs a detection signal I1 (an example of a detection signal) according to the intensity of the received laser light. The laser light transmitted though a standard sample (described later) or a target gas 30 enters the first light receiving apparatus 14. The first light receiving apparatus 14 is typically a photodiode. The signal processing apparatus 16 processes the detection signal I1 outputted from the first light receiving apparatus 14. The signal processing apparatus 16 has a low pass filter 16*a*. The low pass filter 16*a* extracts a direct-current component of the detection signal I1 outputted from the first light receiving apparatus 14. Then, the signal processing apparatus 16 outputs a signal I2 that represents an intensity of the direct-current component extracted with the low pass filter 16*a*.

The first phase-sensitive detection apparatus 18 (an example of an obtaining unit) obtains a second harmonic component (an example of a specific frequency component) that is oscillated at the harmonic frequency ω2 from the detection signal I1 outputted from the first light receiving apparatus 14. The first phase-sensitive detection apparatus 18 includes a lock-in amplifier 18*a* and a low pass filter 18*b*. The lock-in amplifier 18*a* performs a phase-sensitive detection. Specifically, the first phase-sensitive detection apparatus 18 detects, from the detection signal I1 outputted from the first light receiving apparatus 14, a component oscillated at the harmonic frequency ω2. Then, the first phase-sensitive detection apparatus 18 generates a direct-current signal proportional to the component. The lock-in amplifier 18*a*, to which the signal S2 oscillated at the harmonic frequency ω2 is inputted from the frequency amplifier 10, performs a phase-sensitive detection using the signal S2. The low pass filter 18*b* extracts a direct-current component from a signal outputted from the lock-in amplifier 18*a*. Then, the first phase-sensitive detection apparatus 18 outputs a second harmonic signal I3 that represents the direct-current component extracted with the low pass filter 18*b*.

The temperature controller 20 controls a temperature of the light source 2. Since the wavelength of the laser light oscillated by the light source 2 depends on a temperature of a semiconductor laser device used in the light source 2, the temperature controller 20 can control the wavelength of the laser light. The measurement apparatus 22 measures quantities of state of the target gas 30. The quantities of state of the target gas 30 include a temperature, a pressure, and partial pressures of component gases included in the target gas 30. The measurement apparatus generates a signal S3 that represents the measured quantities of state. In the present embodiment, since the measurement apparatus 22 measures the temperature of the target gas 30, the signal S3 represents the temperature of the target gas 30.

The computer 40 processes the signals outputted from the apparatuses included in the gas measurement apparatus 1. The computer 40 is an example of a controlling apparatus. To the computer 40, inputted are the signal I2 outputted from the signal processing apparatus 16, the second harmonic signal I3 outputted from the first phase-sensitive detection apparatus 18, and the signal S3 outputted from the measurement apparatus 22. The computer 40 also controls the wave generating unit 24. Specifically, the computer 40 is connected to the constant current generating apparatus 4, the first wave generator 6, the second wave generator 8, and the wave mixer 12 such that they can send and receive the signals. The computer 40 then controls these apparatuses.

1.2 Computer

Next, the computer 40 will further be explained referencing FIG. 2. FIG. 2 shows a block diagram of functioning units of the computer 40. The computer 40 includes a Central Processing Unit (CPU), a Read Only Memory (ROM), and a Random Access Memory (RAM), which are not shown in the figure. The CPU executes a program stored in the ROM and a process is performed in accordance with the program. Functions of the functioning units explained below are fulfilled by processes based on programs.

The computer 40 includes a recorder 41, a R calculating unit 42, a comparing unit 43, a setting unit 44, a temperature determination unit 45, a concentration measurement unit 46, and a memory unit 47. The computer 40 also includes a storage medium reader 48 that is hardware. To the storage medium reader 48, a storage medium 50 can be installed. The storage medium reader 48 can read and write information from/to the storage medium 50. The storage medium 50 can be removed from the computer 40 and record programs and/or data. A display 60 and an input device 70 are connected to the computer 40.

The recorder 41 records values of the second harmonic component. To the recorder 41, inputted are the second harmonic signal I3 outputted from the first phase-sensitive detection apparatus 18. The recorder 41 determines the value of the second harmonic component based on the second harmonic signal I3. The recorder 41 records the direct-current component of the detection signal I1. The recorder 41 inputs the signal I2 outputted from the signal processing apparatus 16. The recorder 41 determines the direct-current component of the detection signal I1 from the signal I2. The R calculating unit 42 (an example of a calculating unit) reads the value of the second harmonic component recorded by the recorder 41 and calculates the peak-bottom ratio R. The peak-bottom ratio R will be explained later.

The comparing unit 43 compares the peak-bottom ratio R calculated by the R calculating unit 42, with a target value. The target value will be explained later. The setting unit 44 (an example of a setting unit) outputs the control signal S4 for varying the intensity of the modulation current when the peak-bottom ratio R is different from the target value (refer to FIG. 1).

The temperature determination unit 45 determines the temperature of the target gas 30 based on the signal S3 outputted from the measurement apparatus 22. The concentration measurement unit 46 determines a concentration of a target component of the target gas 30 based on the signal I2 outputted from the signal processing apparatus 16, the second harmonic signal I3 outputted from the first phase-sensitive detection apparatus 18, and the temperature of the target gas 30 determined by the temperature determination unit 45. The memory unit 47 keeps information required for an operation of the gas measurement apparatus 1. The target value to be compared with the peak-bottom ratio R by the comparing unit 43 is recorded in the memory unit 47. In the memory unit 47, a relationship between an absorption coefficient of the target component, a pressure, and a temperature is recorded in advance. In the present embodiment, the memory unit 47 is ROM.

The display 60 displays statuses of the gas measurement apparatus 1 and information required to operate the gas measurement apparatus. The input device 70 is used for inputting information required to operate the gas measurement apparatus 1. In the present embodiment, the input device 70 is a keyboard. However, the input device 70 may be other devices such as a touch panel because any devices that can input operations can be used as the input device 70.

1.3 A Setting Method of a Width of Wavelength Modulation

Figure 3:
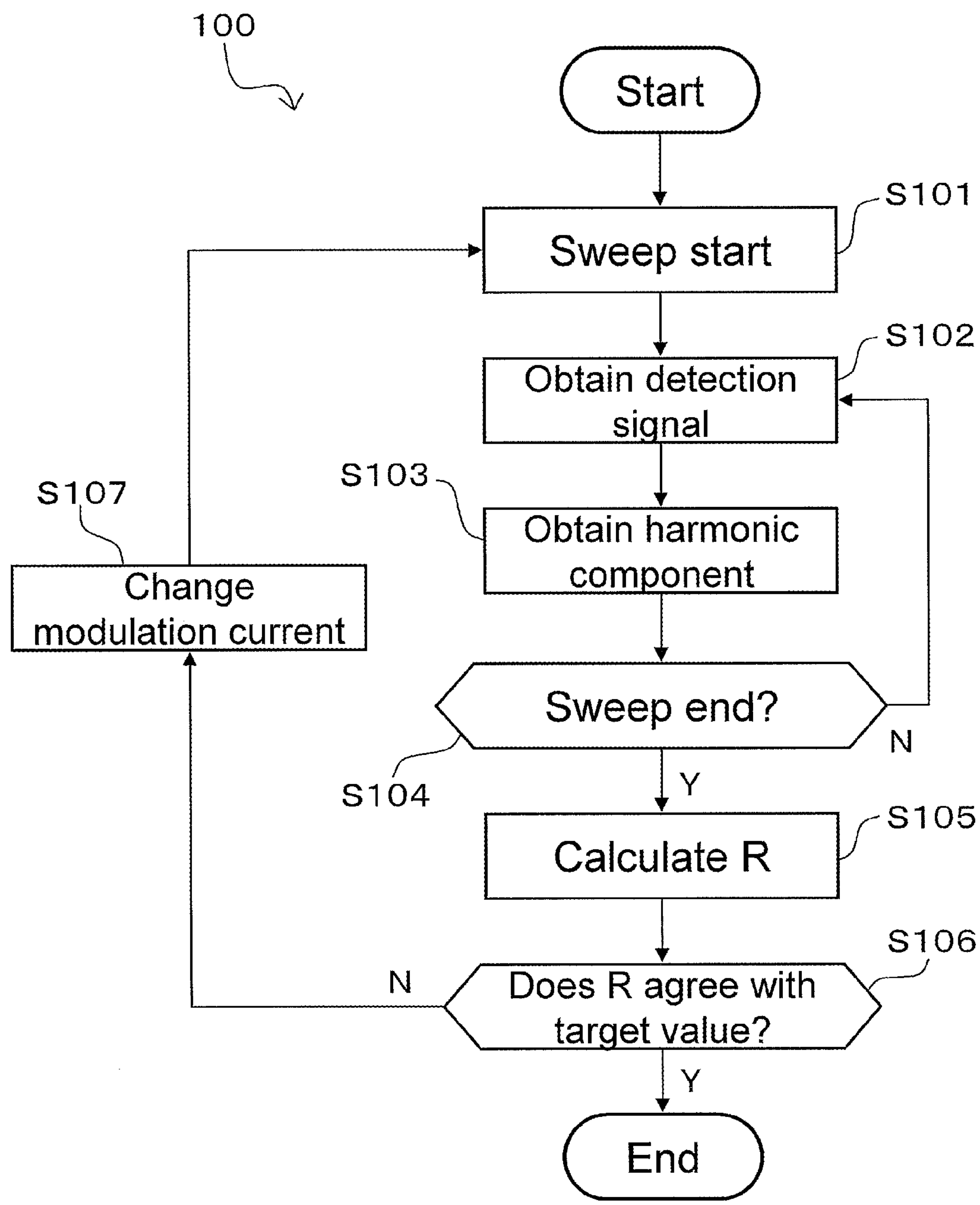
FIG. 3 is a flowchart that shows a method of setting a width of wavelength modulation according to a first embodiment.

Next, referencing FIG. 3, a method of setting a width of wavelength modulation in the gas measurement apparatus 1 will be explained. FIG. 3 shows a flow 100. The flow 100 includes steps S101 to S107. In the present embodiment, the setting of a width of wavelength modulation is performed as an initial adjustment of the gas measurement apparatus 1. At a point when the setting of the width of wavelength modulation starts, the target gas is replaced by the standard sample. For the standard sample, the peak-bottom ratio with which a desired width of wavelength modulation can be determined is known in advance. The peak bottom ratio with which the desired width of wavelength modulation can be determined is recorded in the memory unit 47 in advance. It should be noted that the standard sample is a calibration gas that has predetermined pressure, temperature, and concentration. The calibration gas includes a gas component to be measured (namely, a target component) and a concentration of the gas component in the standard sample is known.

In step S101, a sweep starts. Specifically, an intensity of the ramp current outputted from the first wave generator 6 starts to increase from its minimum value (namely, a base level current). Thus, an intensity of the main current changes slower than that of the modulation current. The driving current that includes the main current and the modulation current is inputted to the light source 2. Then, the light source 2 oscillates the laser light in accordance with the driving current. The laser light oscillated by the light source 2 is transmitted into the standard sample. The laser light transmitted through the standard sample impinges to the first light receiving apparatus 14.

In step S102, the first light receiving apparatus 14 obtains the detection signal I1. The detection signal I1 is inputted to the signal processing apparatus 16 and the first phase-sensitive detection apparatus 18. The signal processing apparatus 16 obtains the signal I2 that represents the direct-current component of the detection signal I1.

In step S103, the first phase-sensitive detection apparatus 18 obtains the second harmonic signal I3 from the detection signal I1. The second harmonic signal I3 is inputted to the recorder 41 of the computer 40. Then, the recorder 41 records the second harmonic component.

In step S104, it is determined whether the sweep with the ramp current ends or not. The sweep ends when one period of the ramp current ends. An intensity of the ramp current has a minimum value at the starting point of the sweep and a maximum value at the end of the sweep. When the sweep ends, the flow proceeds to step S105. When the sweep has not ended yet, the flow goes back to step S102. Since the modulation frequency ω1 is larger than a frequency of the ramp current (an inverse of a period of the sweep), a derivation of the second harmonic component is performed plural times during one sweep. Namely, a string of values of the second harmonic component is obtained with the sweep. In the present embodiment, a timing to obtain the values of the second harmonic component is controlled by the computer 40.

Figure 4B:
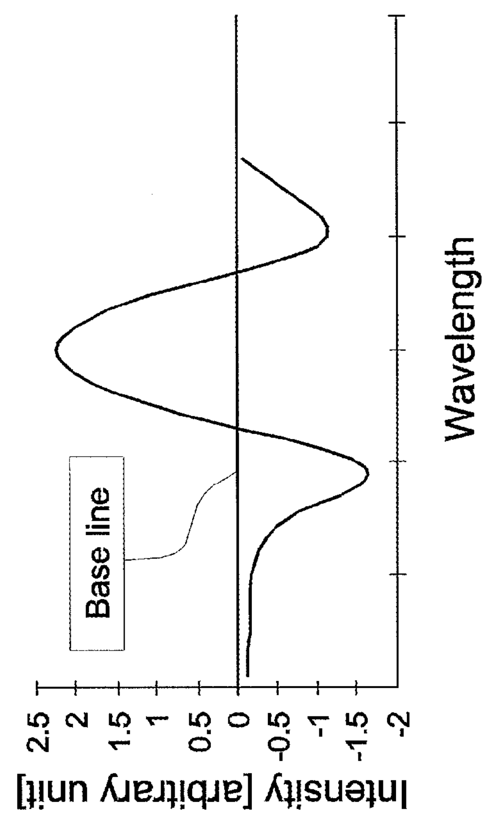
FIG. 4(B) is a graph that shows an example of a second harmonic component in case of water vapor (width of wavelength modulation: 0.21 nm).
Figure 4A:
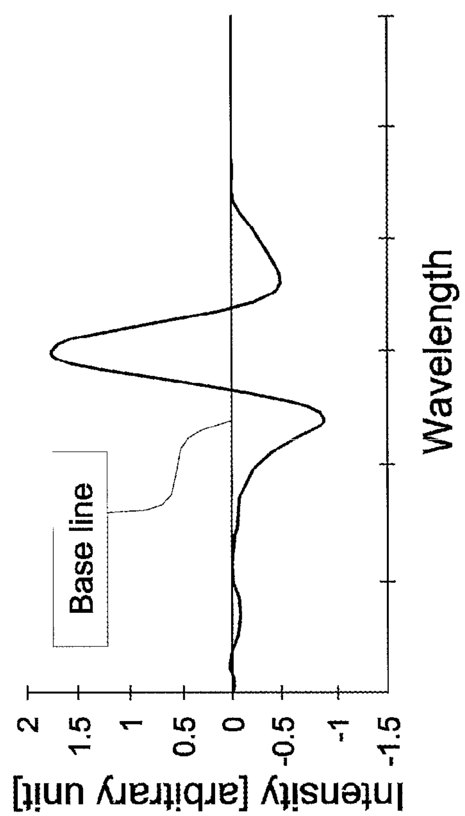
FIG. 4(A) is a graph that shows an example of a second harmonic component in case of water vapor (width of wavelength modulation: 0.09 nm)

FIGS. 4(A) and (B) show graphs of the second harmonic components. The width of wavelength modulation was 0.12 nm when the second harmonic component shown in FIG. 4(A) was obtained. The width of wavelength modulation was 0.18 nm when the second harmonic component shown in FIG. 4(B) was obtained. As shown in these figures, shapes of the graphs change depending on the magnitude of the width of wavelength modulation. Factors that can influence the shape of the graph of the second harmonic component are temperature, pressures, and partial pressures of coexisted gases of the target gas 30, in addition to the width of wavelength modulation. The same can be said in a case of other harmonic components and a first harmonic component. It should be noted that horizontal axes in FIGS. 4(A) and (B) represent wavelength. As long as the string of the values of the second harmonic component can be obtained, the value of the wavelength in the graph may not necessarily be specified as the exact central wavelengths where each value of second harmonic component in the string of the values of the second harmonic component is obtained.

Figure 5:
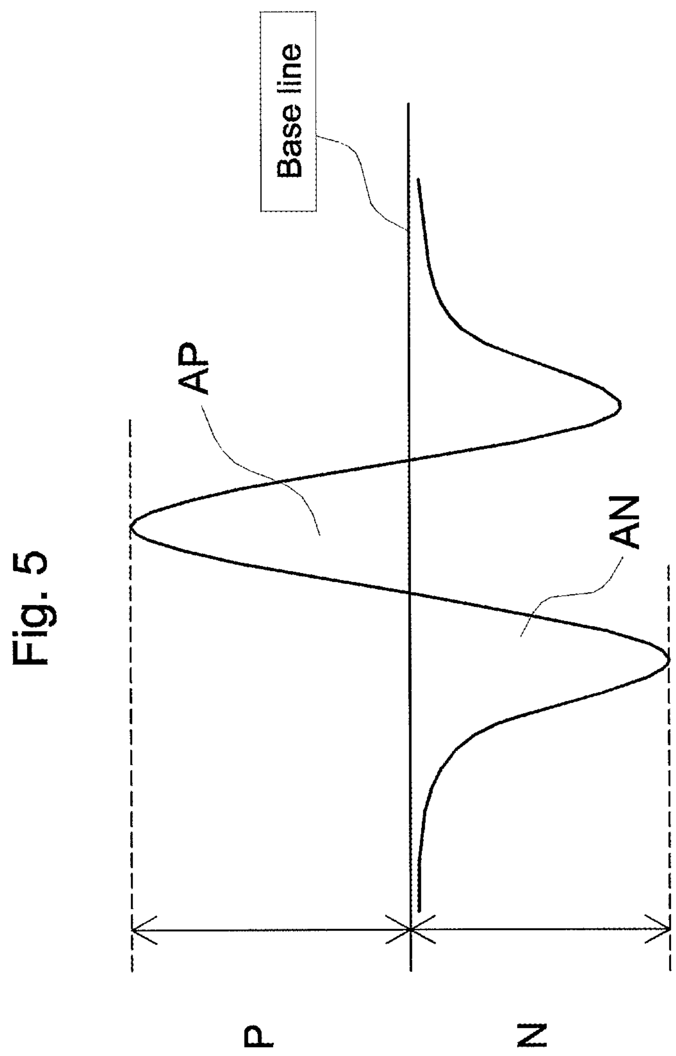
FIG. 5 is a graph that shows an example of a second harmonic component.

In step S105, the R calculating unit 42 calculates the peak-bottom ratio R. The peak-bottom ratio R is a ratio of a magnitude of a local minimum and a magnitude of a local maximum of the second harmonic component. FIG. 5 shows a local maximum and a local minimum in the second harmonic component. The magnitude of the local maximum of the second harmonic component is a distance P between a base line and a peak at the positive side. The magnitude of the local minimum of the second harmonic component is a distance N between a base line and a peak at the negative side. The peak-bottom ratio R is then calculated by P/N. It should be noted that magnitudes of local maxima and local minima of a first and higher harmonic component can be specified in the same manner.

In step S106, the comparing unit 43 compares the peak-bottom ratio R with the target value. Specifically, the comparing unit 43 reads the target value out of the memory unit 47 and compares it with the peak-bottom ratio R. If the peak-bottom ratio R equals to the target value, namely, the difference between these values is within a predetermined allowable range, the setting of the width of wavelength modulation ends. Thus, it is a condition to end the setting of the width of wavelength modulation that the peak-bottom ratio R equals to the predetermined target value (an example of a predetermined condition). If the peak-bottom ratio R does not equal to the target value, the flow proceeds to step S107.

In step S107, the intensity of the modulation current is changed. Specifically, the setting unit 44 outputs the control signal S4 for changing the intensity of the modulation current. The control signal S4 is inputted to the second wave generator 8. The second wave generator 8 outputs the modulation current in which its intensity is changed in accordance with the control signal S4. Thus, the setting unit 44 sets the width of wavelength modulation by changing the intensity of the modulation current. After changing the intensity of the modulation current, the sweep starts again in step S101. The steps S101 to S107 are performed repeatedly until the peak-bottom ratio R equals to the target value.

1.4 Relationship Between Widths of Wavelength Modulation and Second Harmonic Components Here, the relationship between the width of wavelength modulation and the second harmonic component will be explained. The peak-bottom ratio R corresponds to the width of wavelength modulation in one-to-one. The peak-bottom ratio R is also an example of an index quantity that characterizes the second harmonic component. Since the width of wavelength modulation can be made corresponding to the intensity of the modulation current, the peak-bottom ratio R also corresponds to the intensity of the modulation current in one-to-one.

Figure 6A:
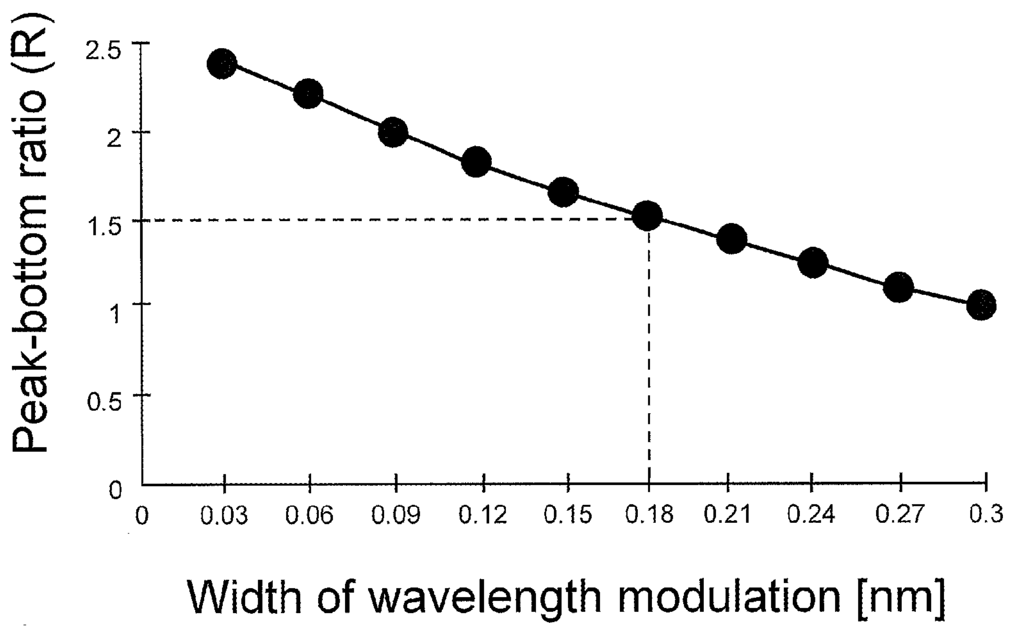
FIG. 6(A) is a graph that shows a relationship between a width of wavelength modulation and a peak-bottom ratio in a case of ammonia vapor and FIG. 6(B) is a graph that shows a relationship between a width of wavelength modulation and an intensity of a second harmonic component (P+N values) in a case of ammonia vapor.
Figure 6B:
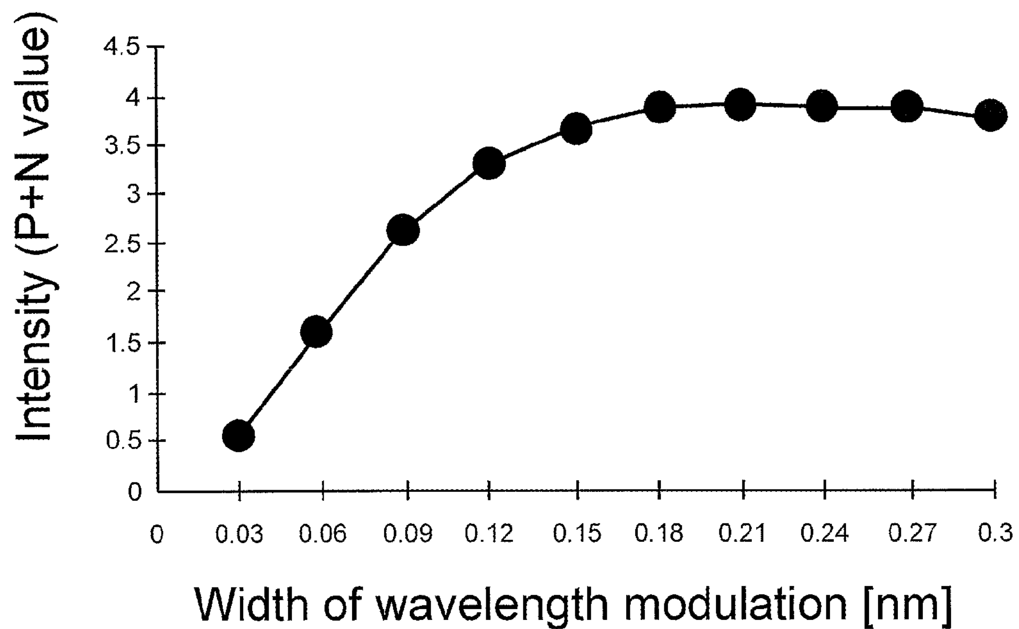

FIG. 6(A) shows, as an actual example, the relationship between the width of wavelength modulation and the peak-bottom ratio R. Specifically, FIG. 6(A) shows a result when the peak-bottom ratio R of the second harmonic component of ammonia vapor was measured, with the width of wavelength modulation being varied. As shown in FIG. 6(B), the magnitude of the second harmonic component also depends on the width of wavelength modulation. FIG. 6(B) shows a result when the magnitude of the second harmonic modulation was measured, with the widths of wavelength modulation being varied. A vertical axis of FIG. 6(B) represents the P+N value and the magnitude of the second harmonic component is represented by the P+N value. Here, the P+N value is a difference between the extreme value of the second harmonic component at the positive side from the base line and that at the negative side from the base line, namely, a sum of the distances P and N. It should be noted that, when deriving FIGS. 6(A) and (B), only the widths of wavelength modulation were changed while pressure, temperature, and concentration of ammonia vapor were kept constant.

Figure 7A:
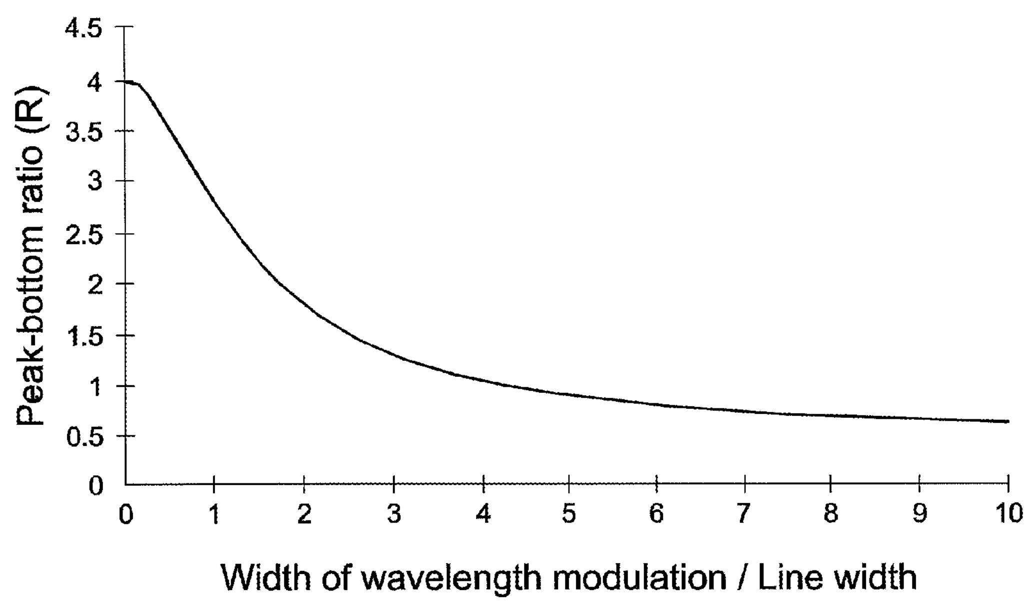
FIG. 7(A) is a graph that shows a relationship between a width of wavelength modulation and a peak-bottom ratio R in a case of Lorentzian absorption line and FIG. 7(B) is a graph that shows a relationship between a width of wavelength modulation and an intensity of a second harmonic component (P+N values) in a case of Lorentzian absorption line.
Figure 7B:
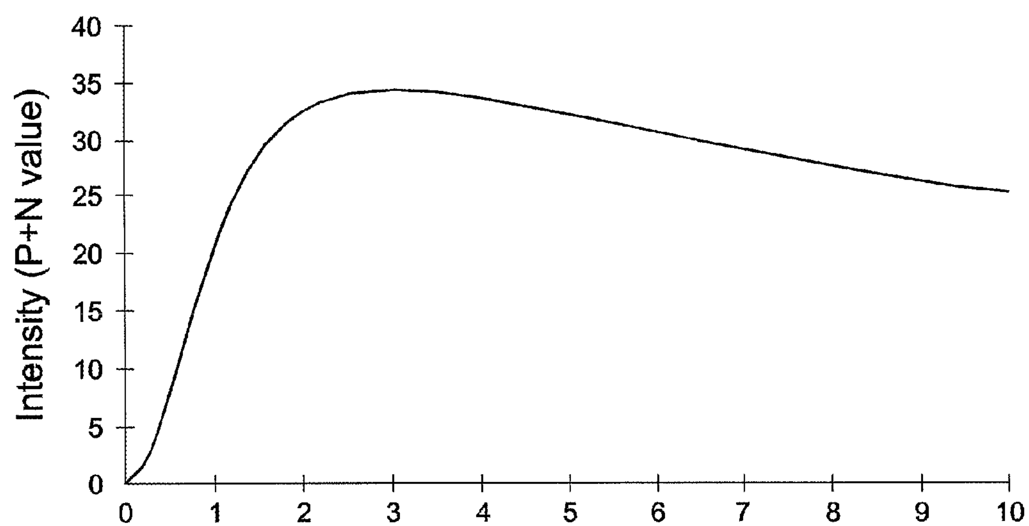

A theoretical model also shows that the peak-bottom ratio R corresponds to the width of wavelength modulation in one-to-one. According to a theory, the shape of the absorption line depends on the pressure and the absorption line governed by the pressure becomes a Lorentzian-type line. The shape of the absorption line also depends on a Doppler effect due to velocities of gas molecules and the shape of the absorption line governed by the Doppler effect becomes a Gaussian-type line. FIG. 7(A) shows the relationship between the width of wavelength modulation and the peak-bottom ratio R in the case where the absorption line is a Lorentzian-type spectrum. FIG. 7(B) shows the relationship between the width of wavelength modulation and the P+N value of a second harmonic component in the case where the absorption line is a Lorentzian-type line. It should be noted that the width of wavelength modulation was changed in broader ranges in FIGS. 7(A) and (B) than in FIGS. 6(A) and (B). It should also be noted that the horizontal axes in FIGS. 7(A) and (B) represent values that are obtained by dividing the width of wavelength modulation by a line width of the absorption line. Here, the line width is a value that is half of a half-width of the absorption line.

As shown in FIG. 7(A), the peak-bottom ratio R can be made corresponding to the width of wavelength modulation in one-to-one. As also shown in FIG. 7(B), the P+N value of the second harmonic component depends on the width of wavelength modulation. Since the larger the P+N value of the second harmonic component is, the more an S/N ratio in the measurement of the intensity improves, the width of wavelength modulation may be set such that the P+N value of the second harmonic component becomes large.

On the other hand, the intensity of harmonic components changes by changing a pressure. Therefore, the width of wavelength modulation may be determined based on a fluctuation rate of the harmonic components in the case where a pressure of the standard sample is varied.

Figure 8A:
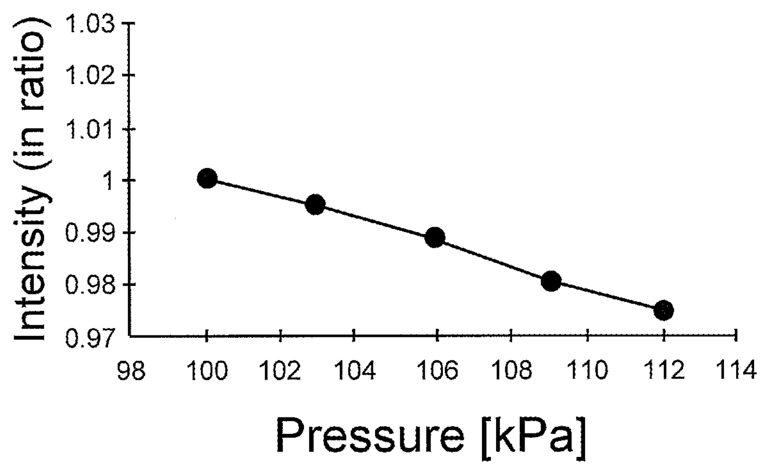
FIG. 8(A) is a graph that shows a relationship between a pressure and an intensity of a second harmonic component in a case of ammonia vapor (width of wavelength modulation: 0.12 nm)
Figure 8B:
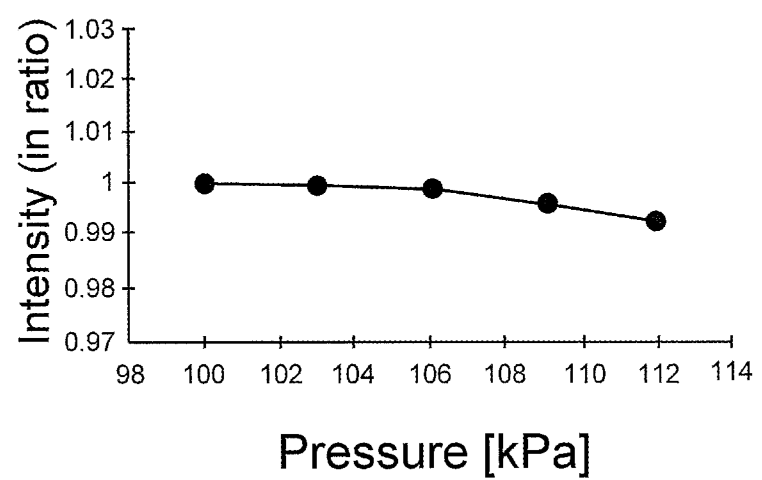
FIG. 8(B) is a graph that shows a relationship between a pressure and an intensity of a second harmonic component in a case of ammonia vapor (width of wavelength modulation: 0.18 nm)
Figure 8C:
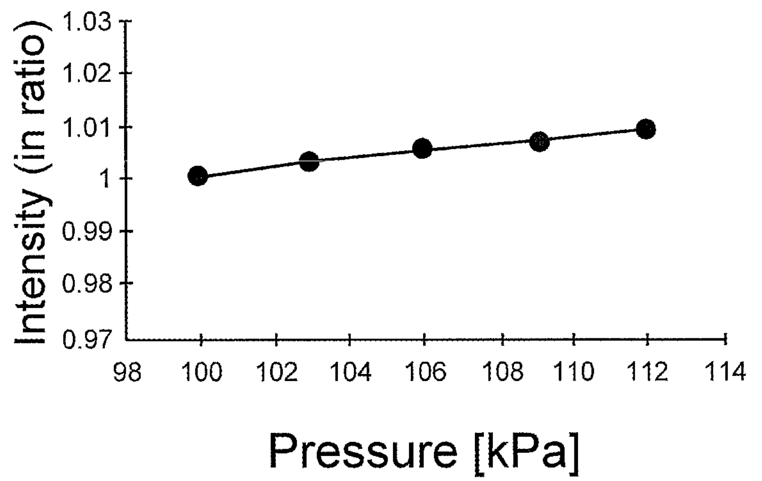
FIG. 8(C) is a graph that shows a relationship between a pressure and an intensity of a second harmonic component in a case of ammonia vapor (width of wavelength modulation: 0.21 nm).

FIGS. 8(A) to (C) show the results of the fluctuations of the second harmonic components in the case of ammonia vapor that were measured, with the pressure being varied. FIG. 8(A) shows the result when the width of wavelength modulation was set to 0.12 nm. FIG. 8(B) shows the result when the width of wavelength modulation was set to 0.18 nm. FIG. 8(C) shows the result when the width of wavelength modulation was set to 0.21 nm. In these graphs, the intensities of the second harmonic components are shown as relative values that are unity when the intensities are measured at a pressure of 100 kPa.

As shown in FIG. 8(A), in the case where the width of wavelength modulation was 0.12 nm, the fluctuation rate of the second harmonic component was 2.5% when the pressure was varied from 100 kPa to 112 kPa. As shown in FIG. 8(B), in the case where the width of wavelength modulation was 0.18 nm, the fluctuation rate of the second harmonic component was 0.8%. As shown in FIG. 8(C), in the case where the width of wavelength modulation was 0.21 nm, the fluctuation rate of the second harmonic component was 1%.

According to the results shown in FIGS. 8(A) to (C), in the present example, the fluctuation rate of the second harmonic component to the pressure become small by setting the width of wavelength modulation to 0.18 nm. By minimizing the influence of the fluctuation of the pressure on the second harmonic component, the intensity of the second harmonic component needs not to be calibrated when measuring the concentration of the target component. Here, the fluctuation rate of the peak intensity of the second harmonic component is preferably 1% or less, more preferably, 0.5% or less when the pressure fluctuates in the range of 10% in magnitude. An example of a representative standard pressure is atmospheric pressure (101 kPa). More specifically, when the pressure fluctuates in the range of 101±10 kPa, the fluctuation rate of the peak intensity of the second harmonic component is preferably 1% or less, more preferably, 0.5% or less. If the fluctuation rate of the peak intensity of the second harmonic component is 1% or less, the concentration of the target gas can be measured accurately even when the intensity of the second harmonic component is not adjusted in accordance with the pressure.

Referencing FIG. 6(B), it is also found that the P+N value of the second harmonic component is large when the width of wavelength modulation is 0.18 nm. Therefore, in the present example, a good S/N ratio can be obtained by setting the width of wavelength modulation to 0.18 nm. It is found, in referencing FIG. 6(A), that the peak-bottom ratio (an example of a target value) is 1.5. Therefore, the width of wavelength modulation can be set to 0.18 nm by adjusting the intensity of the modulation current so that the peak-bottom ratio R is 1.5.

1.5 Measurement of Concentration

Figures 9A, 9B:
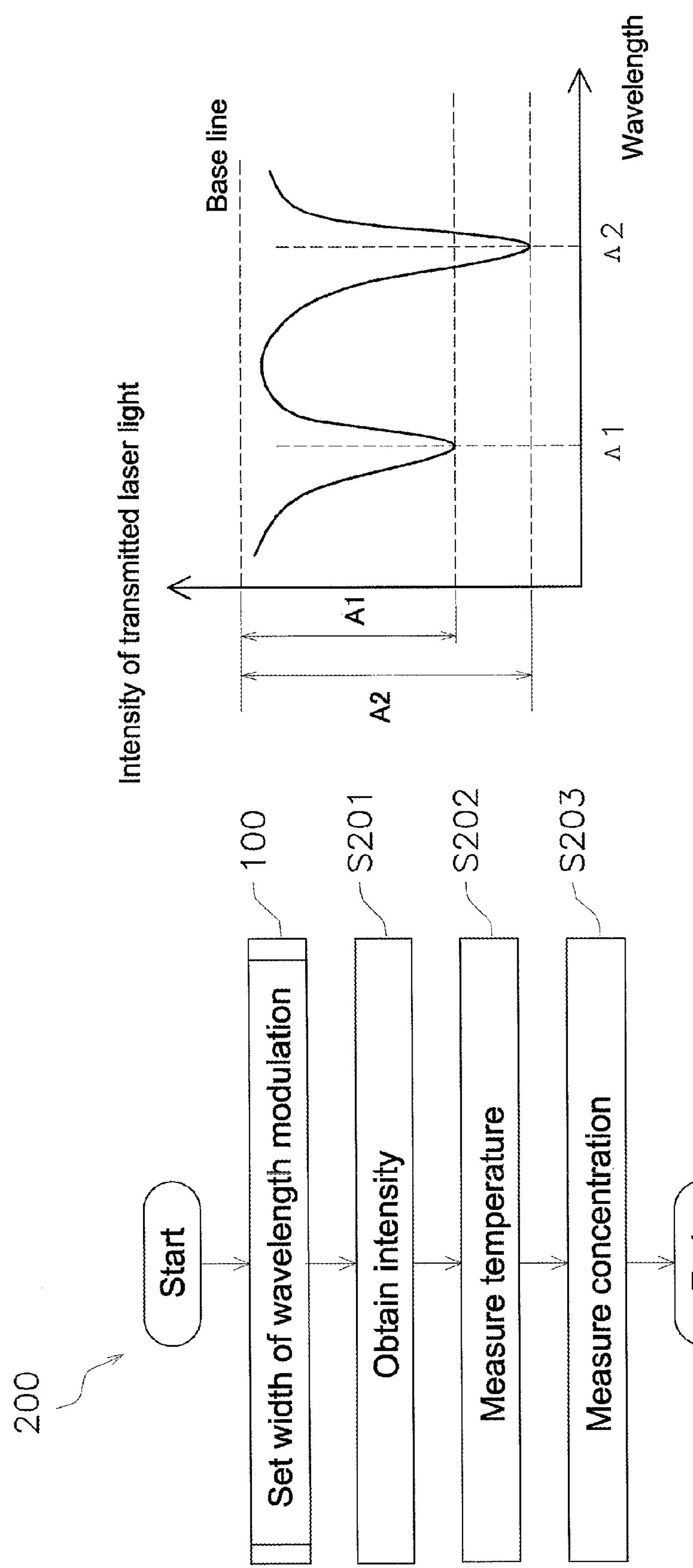
FIG. 9(A) is a flowchart that shows a method of measuring a concentration and FIG. 9(B) is a graph that shows an intensity of a transmitted laser light.

Next, referencing FIG. 9(A), the concentration measurement of the target component of the target gas 30 will be explained. FIG. 9(A) shows a flow 200. The flow 200 comprises the flow 100 and steps S201 to S203. Before performing the flow 200, the target gas is disposed in an optical path of the laser light. Next, the flow 100 is performed and the width of the wavelength modulation is set. Further, the steps S201-S203 are performed successively.

In step S201, the first light receiving apparatus 14 obtains the detection signal I1. Then, the P+N value and the peak intensity of the direct-current component of the detection signal I1 included in the detection signal I1 are detected. Specifically, the sweep with the ramp current is performed and the second harmonic component and the direct-current component of the detection signal I1 are obtained by the recorder 41. Further, the P+N value of the second harmonic component and the peak intensity of the direct-current component of the detection signal I1 are determined.

In step S202, the measurement apparatus 22 measures the temperature of the target gas 30. The signal S3 representing the measured temperature is outputted from the measurement apparatus 22 and inputted to the temperature determination unit 45 of the computer 40. The temperature determination unit 45 determines the temperature of the target gas 30 based on the signal S3.

In step S203, the concentration measurement unit 46 measures the concentration of the target component of the target gas 30. The concentration measurement unit 46 determines the concentration using the P+N value of the second harmonic component and the peak intensity of the direct-current component of the detection signal I1. Generally, the P+N value of the second harmonic component depends on the temperature and pressure of the target gas 30. Therefore, in order to measure the concentration of the target component using the P+N value of the second harmonic component, the P+N value may be adjusted in accordance with the pressure and the temperature. Information related to the target component required for the adjustment is obtained in advance and recorded as data in the memory unit 47. The concentration measurement unit 46 refers to the data recorded in the memory unit 47 and adjusts the P+N value of the second harmonic component in accordance with the temperature determined by the temperature determination unit 45. On the other hand, in the present embodiment, the width of wavelength modulation is chosen to minimize the fluctuation rate of the second harmonic component to the pressure. For this, in adjusting the P+N value of the second harmonic component, the fluctuation of the pressure from the standard pressure is ignored. The concentration measurement unit 46 determines the concentration of the target component based on the adjusted P+N value of the second harmonic component.

1.6 Effects of the First Embodiment

The first embodiment can be expressed as follows.

(1) The gas measurement apparatus according to the first embodiment measures the target gas 30. The gas measurement apparatus comprises the light source 2, the first light receiving apparatus 14, the first phase-sensitive detection apparatus 18, the R calculating unit 42, and the setting unit 44. The light source 2 oscillates the laser light that has the central wavelength determined by the main current and is modulated according to the modulation current, with the central wavelength being varied. The first light receiving apparatus 14 outputs the detection signal I1 according to the intensity of the laser light transmitted through the standard sample. The phase-sensitive detection unit 18 obtains, from the detection signal I1, the second harmonic component oscillated at the harmonic frequency ω2 twice as large as the modulation frequency ω1. The R calculating unit 42 calculates the peak-bottom ratio R of the second harmonic component. The setting unit 44 sets the width of wavelength modulation of the laser light so that the peak-bottom ratio R satisfies the predetermined condition.

In the gas measurement apparatus 1, the width of wavelength modulation is set so that the peak-bottom ratio R, the ratio of the magnitude of the local minimum and the magnitude of the local maximum of the second harmonic component, satisfies the predetermined condition. Therefore, apparatuses or samples for checking the variation of the wavelength of the laser light to the variation of the magnitudes of the modulation current are not required. Thus, works and processes for setting the width of wavelength modulation can be simplified. The time for setting the width of wavelength modulation can also be reduced.

(2) In the first embodiment, the predetermined condition means that the peak-bottom value R corresponding to the width of wavelength modulation in one-to-one equals to the predetermined target value. The setting unit 44 sets the width of wavelength modulation by adjusting the intensity of the modulation current. The peak-bottom ratio R corresponds to the intensity of the modulation current in one-to-one and further the width of wavelength modulation can be specified by determining the intensity of the modulation current. Therefore, by setting the intensity of the modulation current so that the peak-bottom ratio R equals to the predetermined target value, the width of wavelength modulation can be set to have a desired magnitude. Thus, works for setting the width of wavelength modulation can be reduced.

In addition, only two values of the second harmonic component are required as information to calculate the peak-bottom ratio R. Moreover, the accuracy of the peak-bottom ratio R can be maintained as long as accurate data of the second harmonic component are obtained only in the vicinities of the wavelength where the local minimum or the local maximum appears. Therefore, the peak-bottom ratio R can be detected with less process. As the result, the process for setting the width of wavelength modulation can be reduced.

Furthermore, since the peak-bottom ratio R includes information of the values of local minimum and local maximum, the peak-bottom ratio R characterizes the overall shape of the graph of the second harmonic component. Namely, the peak-bottom ratio R is also an example of the index quantity that characterizes the shape of the graph of the second harmonic component. Since the peak-bottom ratio R does not depend on the intensity of the laser light, it can be said that the peak-bottom ratio R is the index quantity that is resistive to the fluctuation of the intensity of the laser light. If the index quantity depends on the intensity of the laser light, the calibration of the intensity of the laser light is required before setting the width of wavelength modulation, thus increasing works. Therefore, by using the peak-bottom ratio R as the index quantity, the calibration of the intensity of the laser light can be omitted in setting the width of wavelength modulation.

(3) The target value is determined based on the fluctuation rate of the second harmonic component when the pressure of the standard sample is varied. Thus, the measurement of the target gas 30 is possible without calibrating the influence of the fluctuation of the pressure from the standard pressure, and the measurement can be simplified.

2. Second Embodiment

In the first embodiment described above, the temperature of the target gas 30 was measured by the measurement apparatus 22. However, in a second embodiment described below, the temperature of the target gas 30 is measured without using the measurement apparatus 22. The gas measurement apparatus 1 according to the second embodiment has substantially the same structure as the gas measurement apparatus 1 according to the first embodiment. However, the process performed in the temperature determination unit 45 in the second embodiment is different from that in the first embodiment.

Specifically, the temperature of the target gas 30 is determined by using the intensity of the transmitted laser light. As shown in FIG. 9(B), the transmitted laser light has the intensity in accordance with the absorption line. In FIG. 9(B), peaks appear at the wavelengths Λ1 and Λ2. It is known that a ratio of intensities of first and second peaks depends on a temperature when a first wavelength at which the first peak appears is different from a second wavelength at which the second peak appears. In FIG. 9(B), a ratio A1/A2, the ratio of the peak intensity A1 at the wavelength Λ1 and the peak intensity A2 at the wavelength Λ2, depends on temperatures. With this characteristic, the temperature of the target gas 30 can be measured. Here, the peak intensity corresponds to the distance between the base line and the tip of the peak.

It is known that the ratio of the first and second peak intensities varies in accordance with the variation of the width of wavelength modulation. It can be the case that the width of wavelength modulation is varied even if the modulation current is kept constant, because the relationship between the modulation current and the width of wavelength modulation varies gradually due to an operation of the laser. In this case, the width of wavelength modulation may be kept constant by adjusting the modulation current, when measuring the temperature using the intensity of transmitted laser light.

With the gas measurement apparatus 1 according to the second embodiment, in step S202, the temperature determination unit 45 determines the temperature of the target gas 30 based on the ratio of the peak intensities of the laser light. On the other hand, the flow 100 is performed and the width of wavelength modulation is set before performing step S202. Thus, the width of wavelength modulation is kept constant. As the result, the temperature of the target gas 30 can be measured accurately.

3. Third Embodiment

In the above-described embodiments, the setting of the width of wavelength modulation was performed, with the target gas 30 being replaced by the standard sample. In a third embodiment described below, the setting of the width of wavelength modulation is performed without the target gas 30 being replaced by the standard sample. It should be noted that, hereinafter, the detailed explanations of the structures of a gas measurement apparatus 3 according to the third embodiment that are the same as those of the gas measurement apparatus 1 according to the first embodiment will be omitted and only the structures different from those of the first embodiment will be explained.

As shown in FIG. 10, the gas measurement apparatus 3 according to the third embodiment comprises a beam splitter 5, a sample gas 7, a second light receiving apparatus 9, a second phase-sensitive detection apparatus 11, and a counter 80. In addition, in the gas measurement apparatus 3, the computer 40 includes a control unit 49. It should be noted that the signal processing apparatus 16 and the measurement apparatus 22 are not drawn in FIG. 10. The gas measurement apparatus 3 also comprises an apparatus (not drawn) configured to extract a direct-current component of a detected signal I4 (described below) outputted from the second light receiving apparatus 9 and to input the direct-current component of the detected signal I4 to the computer 40.

The beam splitter 5 splits the laser light oscillated by the light source 2 into two laser lights. These two laser lights are transmitted into different optical paths. The standard gas 7 (an example of a standard sample) is a gas with which the peak-bottom ratio that can obtain the desired width of wavelength modulation is known. In the present embodiment, the standard gas is also the calibration gas. The second light receiving apparatus 9 (an example of a detection unit) receives the laser light oscillated by the laser source 2 and outputs the detected signal I4 (an example of a detection signal) in accordance with the intensity of the received laser light. The laser light received by the second light receiving apparatus 9 is one of the laser lights split by the beam splitter 5. Another laser light split by the beam splitter 5 is transmitted through the target gas 30 and then into the first light receiving apparatus 14.

The second phase-sensitive detection apparatus 11 obtains a second harmonic component (an example of a specific frequency component) oscillated at the harmonic frequency ω2 from the detected signal I4 inputted from the second light receiving apparatus 9. The second phase-sensitive detection apparatus 11 includes a lock-in amplifier and a low pass filter (not drawn). To the second phase-sensitive detection apparatus 11, the signal S2 oscillated at the harmonic frequency ω2 from the frequency multiplier 10 is inputted. The second phase-sensitive detection apparatus 11 functions in the same way as the first phase-sensitive detection apparatus 18 and outputs a second harmonic signal I5 representing the second harmonic component. The second harmonic signal I5 is inputted to the computer 40. The counter 80 (an example of a counting unit) counts the time (continuation time (an example of a continuation time)) during which a gas measurement has been performed by the gas measurement apparatus 3. The counter 80 can send and receive signals to/from the computer.

Unlike the gas measurement apparatus 1 according to the first embodiment, in the gas measurement apparatus 3, the setting of the width of wavelength modulation is performed by using the standard gas 7, the second light receiving apparatus 9, and the second phase-sensitive detection apparatus 11. Namely, the second light receiving apparatus 9 and the second phase-sensitive detection apparatus 11 function in the same ways as the first light receiving apparatus 14 and the first phase-sensitive detection apparatus 18 in the first embodiment, respectively.

Figure 11:
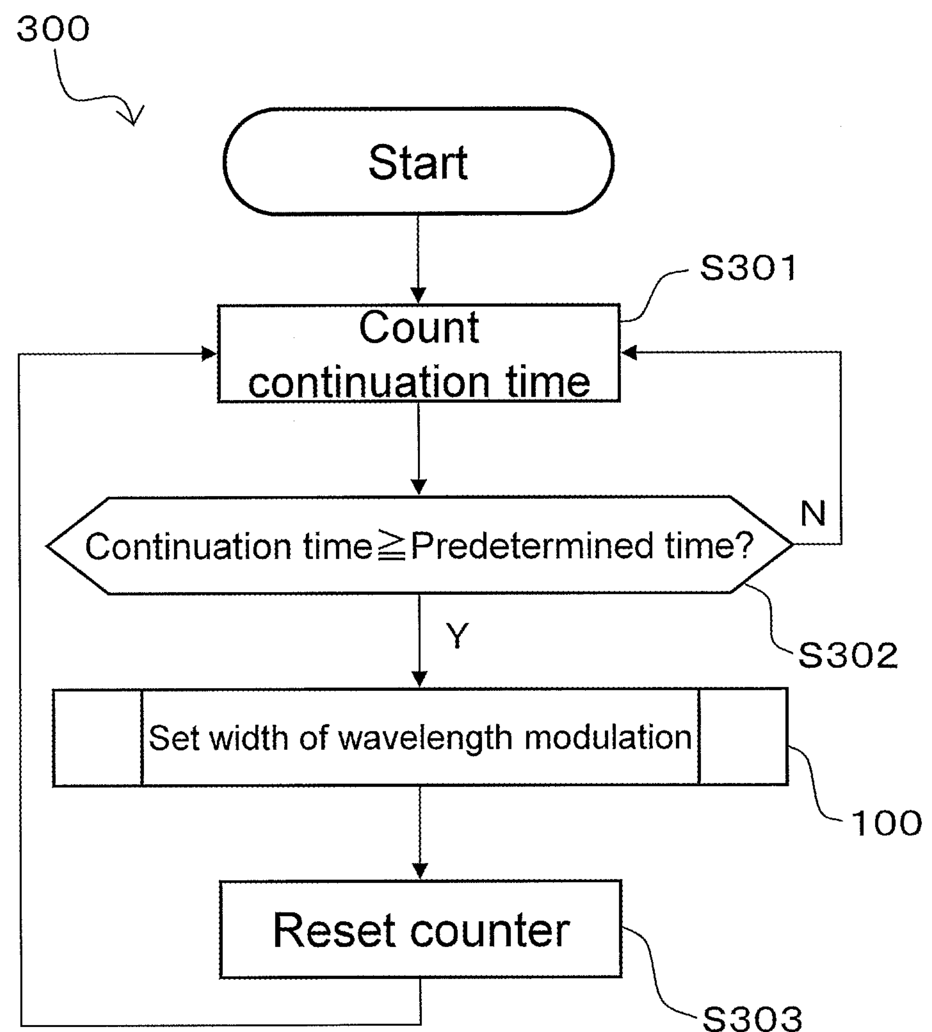
FIG. 11 is a flowchart that shows a method of setting a width of wavelength modulation according to a third embodiment.

Next, referencing FIG. 11, the overall operating flow of the gas measurement apparatus 3 will be explained. FIG. 11 is the flow 300 showing the method of setting the width of wavelength modulation using the gas measurement apparatus 3.

In the gas measurement apparatus 3, the measurements of the target gas are performed continuously. It should be noted that performing the measurements of a gas continuously means that the measurements are performed repeatedly by performing the measurements one after another without stopping the measurements. In step S301, the counter 80 counts the continuation time. The continuation time counted by the counter 80 is inputted to the computer 40.

In step S302, the control unit 49 of the computer 40 determines whether the time counted by the counter 80 (namely, the continuation time) is beyond a regular maintenance period (an example of a predetermined time) or not. The regular maintenance period is set in advance and recorded in the memory of the computer 40. If the condition is satisfied in step S302, the flow 300 proceeds to the flow 100. Otherwise, the flow 300 goes back to step S301. In flow 100, the setting of the width of wavelength modulation is performed in the same manner as the first embodiment. In the present embodiment, the setting unit 44 sets the width of wavelength modulation such that the peak-bottom ratio R equals to the predetermined target value when the continuation time is beyond the predetermined time. In step S303, the counter 80 is reset. When the counter 80 is reset, the flow 300 goes back to step S301. Namely, the continuation time is set to zero when the counter 80 is reset and then the counter 80 restarts counting the continuation time at the time when the counter 80 is reset.

As described above, the method of setting the width of wavelength modulation according to the third embodiment is the method used in the gas measurement apparatus 3. The gas measurement apparatus 3 comprises the light source 2 oscillating the laser light having the central wavelength according to the main current and modulated in accordance with the modulation current, and the first light receiving apparatus 14 outputting the signal in accordance with the intensity of the laser light transmitted through the target gas 30. This method comprises a step of measuring the target gas 30 continuously and determining whether the measurements of the target gas 30 have been performed for the predetermined time or not. This method also comprises a step of obtaining the detection signal I4 from the laser light transmitted through the standard gas 7, with the central wavelength being varied, when the measurements of the target gas 30 have been performed for the predetermined time. This method also comprises obtaining, from the detection signal I4, the second harmonic component oscillated at the harmonic frequency ω2 twice as large as the modulation frequency ω1 and calculating the peak-bottom ratio R. Then, this method also comprises a step of setting the width of wavelength modulation so that the peak-bottom ratio R meets the predetermined condition.

Thus, the gas measurement apparatus 3 performs the setting of the width of wavelength modulation when the measurements of the target gas 30 have been performed for the predetermined time. For this, the width of wavelength modulation can be kept constant even if the gas measurement apparatus 3 is operated for a long time.

4. Fourth Embodiment

In the above-described first embodiment, the quantities of state such as the temperature and pressure of the target gas were measured by the measurement apparatus 22. In addition, in the above-described second embodiment, the temperature of the target gas 30 was measured referring to the ratio of two peaks of the transmitted laser light. In contrast, in a fourth embodiment described below, quantities of state other than the temperature of the target gas 30 are determined without using the measurement apparatus 22.

Figure 12:
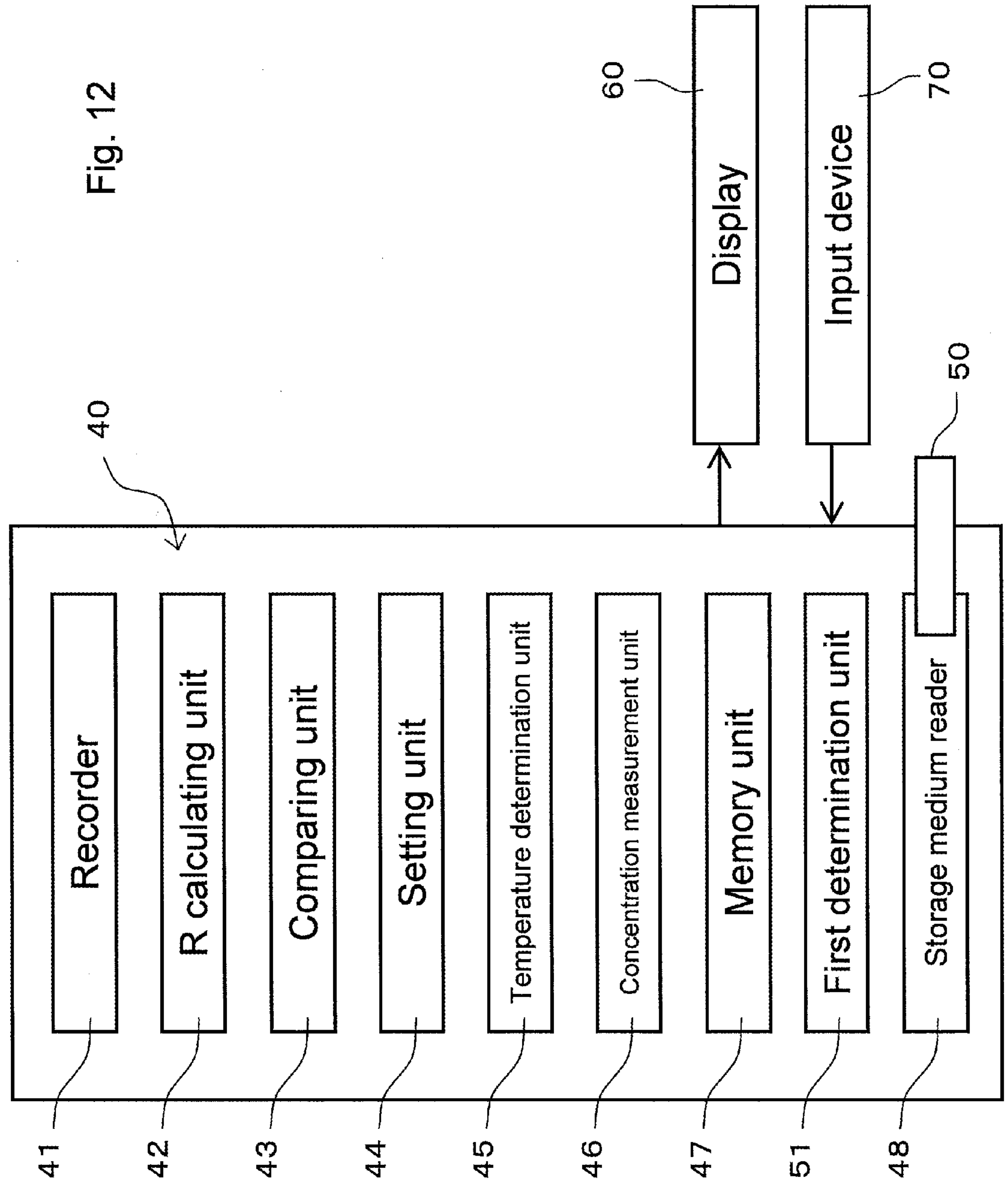
FIG. 12 is a block diagram that shows functioning units of a computer 40 according to a fourth embodiment.

As an example, the method of determining the pressure of the target gas 30 without using the measurement apparatus 22 will be explained below. The gas measurement apparatus 1 according to the fourth embodiment has substantially the same structures as those of the gas measurement apparatus 1 according to the first embodiment. However, as shown in FIG. 12, the computer 40 in the fourth embodiment further includes a first determination unit 51. Hereinafter, the explanation of the structures that is the same as those of the gas measurement apparatus 1 according to the first embodiment will be omitted.

The first determination unit 51 (an example of a determination unit) determines the pressure based on a predetermined relationship between the peak-bottom ratio R and the pressure. More specifically, the first determination unit 51 determines the pressure of the target gas 30 based on a predetermined relationship between the peak-bottom ratio R and a group of quantities of state that determine a state of the target gas 30. In the present embodiment, the group of the quantities of state includes temperature and pressure. The operation of the first determination unit 51 will be explained below.

4.1 Measurement Method of Pressure and Temperature

Figure 13:
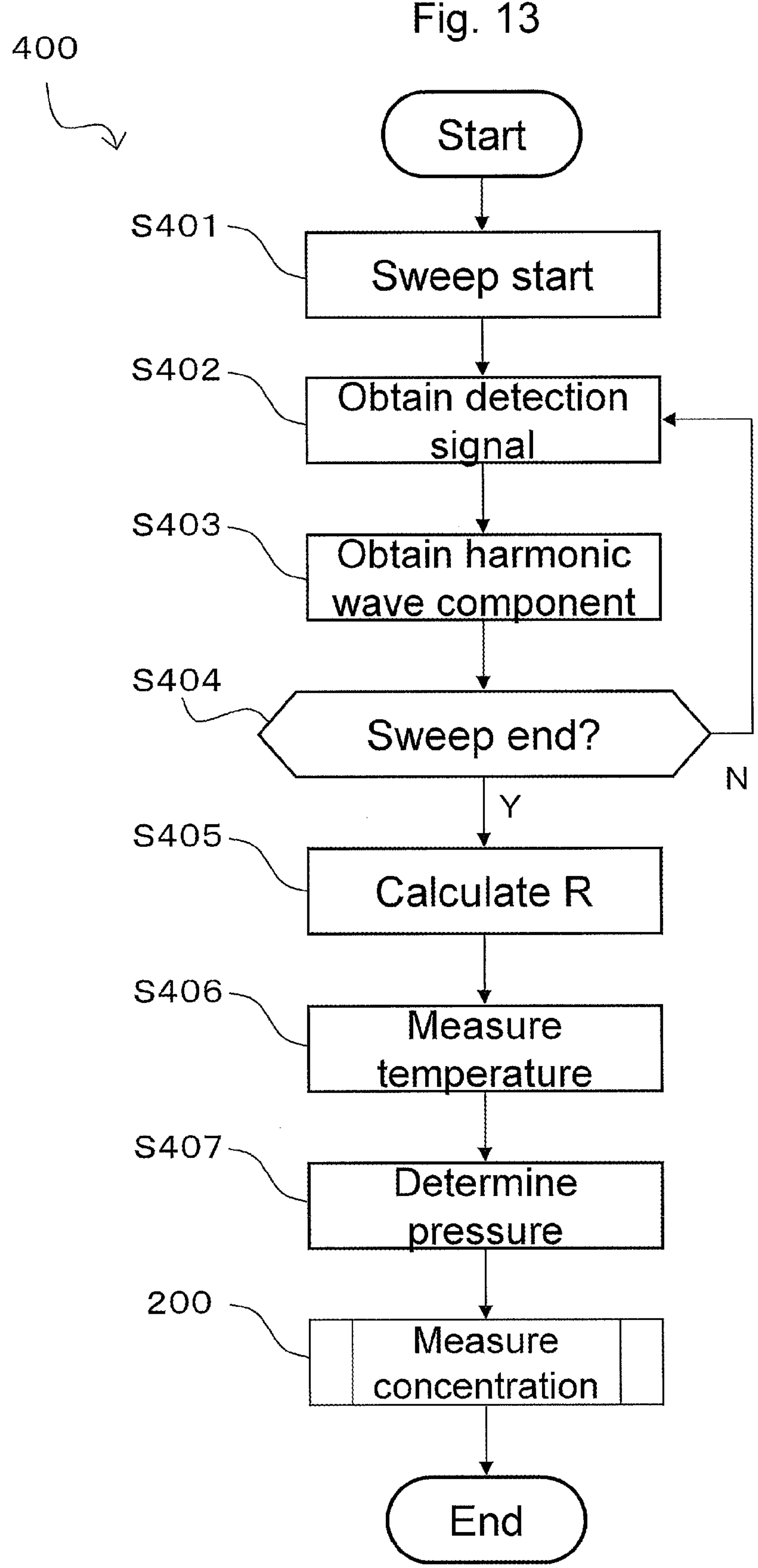
FIG. 13 is a flowchart that shows a determination of a pressure of a target gas according to a fourth embodiment.

Next, referencing FIG. 13, the method of measuring the pressure (an example of a quantity of state) in the gas measurement apparatus 1 according to the fourth embodiment will be explained. FIG. 13 shows the flow 400 of the measurement of the concentration of the target gas 30 and the flow of determining the pressure corresponds to steps S401 to S407.

In step S401, the sweep starts. Specifically, the intensity of the ramp current outputted from the first wave generator 6 starts to increase from its minimum value (namely, the base level current). Thus, the intensity of the main current changes slower than that of the modulation current. The driving current that includes the main current and the modulation current is inputted to the light source 2. Then, the light source 2 oscillates the laser light in accordance with the driving current. The laser light oscillated by the light source 2 is transmitted into the target gas 30. The laser light transmitted through the target gas 30 is transmitted into the first light receiving apparatus 14.

In step S402, the first light receiving apparatus 14 obtains the detection signal I1. The detection signal I1 is inputted to the signal processing apparatus 16 and the first phase-sensitive detection apparatus 18. The signal processing apparatus 16 obtains the signal I2 representing the direct-current component of the detection signal I1.

In step S403, the first phase-sensitive detection apparatus 18 obtains the second harmonic signal I3 from the detection signal I1. The second harmonic signal I3 is inputted to the recorder 41 of the computer 40. Then, the recorder 41 records the second harmonic component.

In step S404, it is determined whether the sweep by the ramp current ends or not. The sweep ends when one period of the ramp current ends. The intensity of the ramp current has the minimum value at the starting point of the sweep and the maximum value at the end of the sweep. If the sweep ends, the flow 400 proceeds to step S405. If the sweep has not ended yet, the flow 400 goes back to step S402. Thus, the derivations of the second harmonic component are performed plural times during one sweep. Namely, the string of the values of the second harmonic component is obtained by the sweep. In the present embodiment, the timing to obtain the values of the second harmonic component is controlled by the computer 40.

Figure 14A:
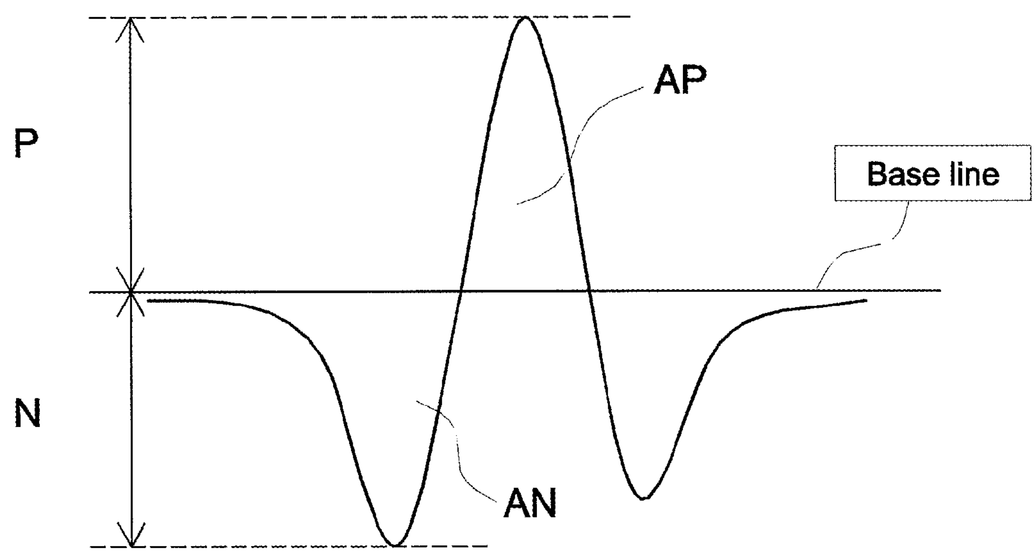
FIG. 14(A) is a graph that shows an example of a second harmonic component and FIG. 14(B) is a graph that shows an example of an absorption line.

FIG. 14(A) shows an example of the second harmonic component. The factors that can influence the shape of the graph of the second harmonic component are the temperature, pressure, partial pressures of coexisted gases of the target gas 30, and width of wavelength modulation. The same can be said in the cases of the higher harmonic components and the first harmonic component. Here, the width of wavelength modulation of the laser light depends on the modulation current. Therefore, the width of wavelength modulation is determined by determining the intensity of the modulation current. The width of wavelength modulation is adjusted in advance to a predetermined value for the measurement of the quantities of state.

Figure 14B:
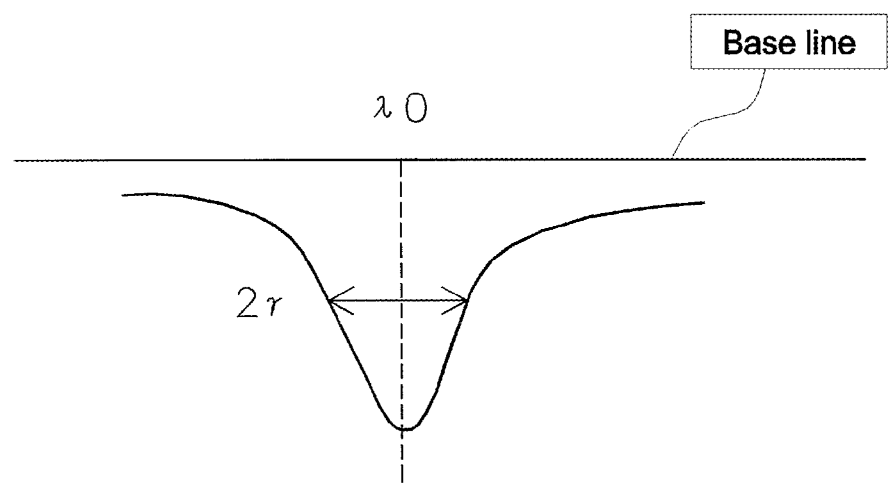

The shape of the graph of the second harmonic component affects the shape of the absorption line of the target gas 30. FIG. 14(B) shows an example of the absorption line. It is known that the shape of the absorption line that is mainly governed by the pressure shows Lorentzian-type line. The absorption line mainly governed by the Doppler effect due to velocities of the gas molecules shows Gaussian-type line. The shape of the absorption line is characterized by the half-width 2γ.

The half-width 2γ depends on the Doppler width due to the Doppler effect and the pressure width due to the pressure. The Doppler width αD of the target component is expressed by the following formula (1), $$\alpha_D = 7.16 \times 10^{-7} \times \nu_0 \sqrt{\frac{T}{M}} \quad \text{Formula 1}$$

where T is the temperature, M is the molecular weight of the target component, and $\nu_0$ is the central wave number that is the inverse of the peak wavelength $\lambda_0$ where the peak of the absorption line appears. On the other hand, the pressure width $\alpha_P$ is expressed by the following formula 2, $$\alpha_P = \sum_i (\gamma_i \times P_i) \quad \text{Formula 2}$$

where $\gamma_i$ is the inherent constant to the coexisted gas $G_i$, $P_i$ is the partial pressure of the coexisted gas $G_i$. The target component is one of the coexisted gases and the contribution of the target gas itself is added to $\alpha_p$. Thus, the shape of the absorption line depends on the pressure, temperature, and the partial pressures of the coexisted gases.

In step S405, the R calculating unit 42 calculates the peak-bottom ratio R. The peak-bottom ratio R is the ratio of the magnitudes of the local maximum and the local minimum of the second harmonic component. FIG. 14(A) shows the local maximum and local minimum of the second harmonic component. The magnitude of the local maximum is the distance P between the base line and the peak at the positive side from the base line. The magnitude of the local minimum of the second harmonic component is the distance N between the base line and the peak at the negative side from the base line. Then, the peak-bottom ratio is calculated by P/N. It should be noted that the magnitudes of the local maxima and local minima can be specified in the same manner as described above in cases of the first harmonic component and the third or higher harmonic components. The magnitude of the second harmonic component can be expressed by the P+N value which is the sum of the distances P and N.

In step S406, the measurement apparatus 22 (an example of a measurement unit) measures the temperature (an example of a measurable quantity of state) of the target gas 30. The signal S3 outputted from the measurement apparatus 22 is inputted to the temperature determination unit 45 of the computer 40. The temperature determination apparatus 45 determines the temperature of the target gas 30 based on the signal S3.

Figure 15A:
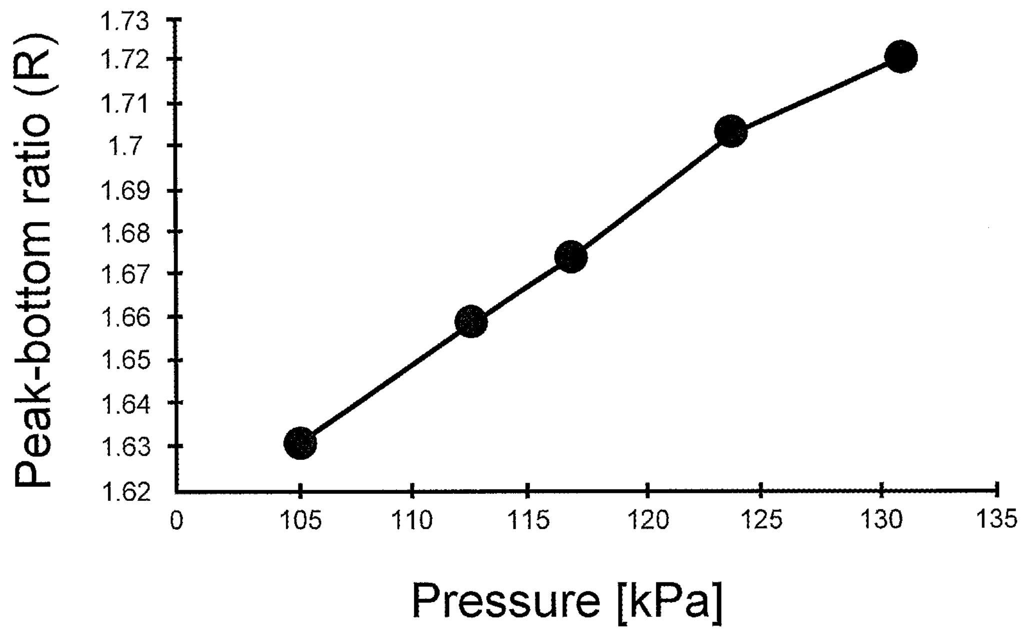
FIG. 15(A) is a graph that shows a relationship between a pressure and an intensity of a second harmonic component in a case of water vapor (width of wavelength modulation: 0.15 nm)

In step S407, the first determination unit 51 measures the pressure of the target gas 30. The first determination unit 51 determines the pressure of the target gas 30 based on the relationship between the peak-bottom ratio R, the temperature, and pressure of the target gas 30. Here, referencing FIGS. 15(A) to 16, the relationship between the peak-bottom ratio R, the pressure, and temperature will be explained. FIG. 15(A) shows the result of the measured peak-bottom ratio R of the second harmonic component of water vapor, which is the target component, with the pressure being varied, under the condition where the temperature, composition ratio of the coexisted gases of the target gas 30, and width of wavelength modulation are constant. As shown in FIG. 15(A), the peak-bottom ratio R changes as the pressure changes. In addition, in the range of the pressure shown in the figure, the peak-bottom ratio R corresponds to the pressure in one-to-one. Therefore, the pressure of the target gas 30 can be determined using the relationship shown in FIG. 15(A) by measuring the peak-bottom ratio R, under the condition where the temperature, composition ratio of the coexisted gases of the target gas 30, and width of wavelength modulation are constant.

Figure 15B:
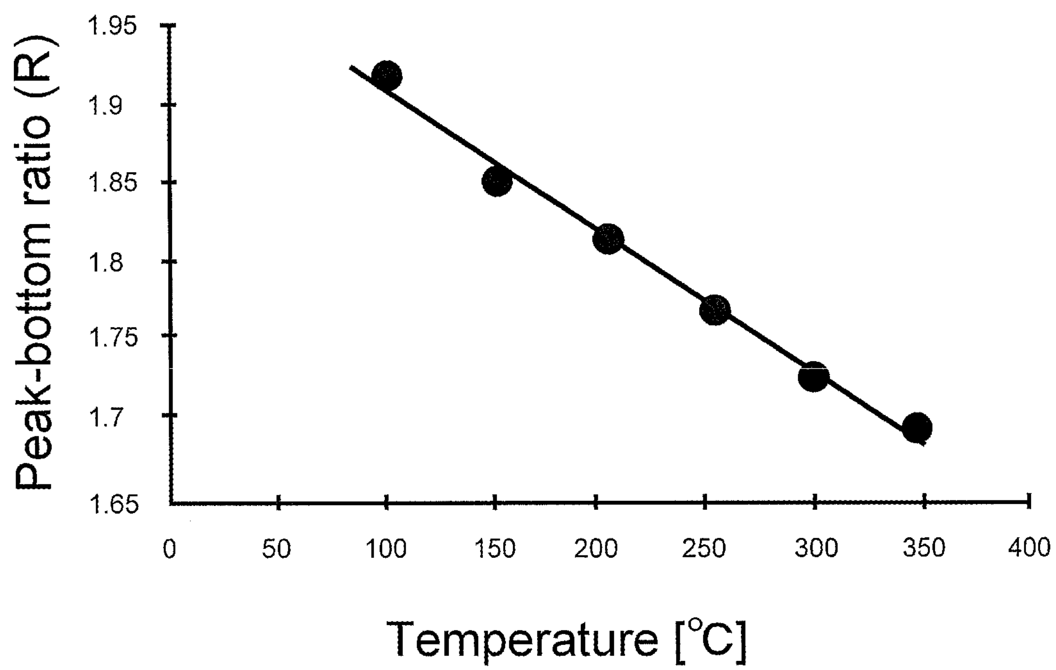
FIG. 15(B) is a graph that shows a relationship between a temperature and an intensity of a second harmonic component in a case of water vapor.

On the other hand, FIG. 15(B) shows the result of the measured peak-bottom ratio R of the second harmonic component of water vapor, which is the target component, with the temperature being varied, under the condition where the temperature, composition ratio of the coexisted gases of the target gas 30, and width of wavelength modulation are constant. As shown in FIG. 15(B), the peak-bottom ratio R changes as the temperature changes. In addition, in the range of the temperature shown in the figure, the peak-bottom ratio R corresponds to the temperature in one-to-one. Therefore, the temperature of the target gas 30 can be determined using the relationship shown in FIG. 15(B) by measuring the peak-bottom ratio R, under the condition where the temperature, composition ratio of the coexisted gases of the target gas 30, and width of wavelength modulation are constant.

FIG. 16 shows the predetermined relationship between the peak-bottom ratio R, temperature, and pressure. In FIG. 16, $T_k$ (k is a subscript and a positive integer) represents the temperature, $Q_l$ (l is a subscript and a positive integer) represents the pressure. Then, $R_{kl}$ represents the peak-bottom ratio R. According to the relationship shown in FIG. 16, the peak-bottom ratio $R_{kl}$ of the second harmonic component of water vapor (namely, the target component) when the temperature of the target gas 30 is $T_k$ and the pressure of the target gas 30 is $Q_l$. For example, when the temperature obtained with the measurement apparatus 22 is $T_3$ and the peak-bottom ratio R calculated from the second harmonic component is R23, the pressure of the target gas 30 is determined to be $Q_2$. It should be noted that it may be the case that the temperature measured by the measurement apparatus 22 and the peak-bottom ratio R do not perfectly agree with any of the temperatures $T_k$ and the peak-bottom ratios $R_{kl}$, respectively. In this case, the pressure can be obtained by interpolation.

The relationship (an example of a predetermined relationship) shown in FIG. 16 is obtained in advance by measuring a standard sample and recorded in the memory unit 47 as data. The standard sample is a sample including the target component. In the present embodiment, the standard gas is a calibration gas and includes the target component. The peak-bottom ratio R of the second harmonic component is measured, while keeping the width of wavelength modulation constant and with the pressure and temperature of the standard sample being varied. Then, the measured peak-bottom ratio R is recorded, while being associated with the temperature and pressure when the peak-bottom ratio R is measured. Therefore, the relationship shown in FIG. 16 is the relationship satisfied by the pressure, temperature, and peak-bottom ratio R when the target gas 30 is replaced by the standard sample. Here, the width of wavelength modulation when the peak-bottom ratio R is measured is the same as that when the peak-bottom ratio R of the standard sample is measured.

The composition of the standard sample is adjusted in accordance with the composition of the target gas 30. Among components considered to be included in the target gas 30, the standard sample includes the components that can influence the absorption line of the target component. In the standard sample, the composition ratios of the components that can influence the absorption line of the target component are also adjusted to agree approximately with their composition ratios of the target gas 30. Thus, the relationship between the peak-bottom ratio R, the temperature, and the pressure determined using the standard sample can be applied to the measurement of the target gas 30, even if there is a slight difference in the composition ratios of the components that can influence the absorption line of the target component between the target gas 30 and the standard sample.

In the example shown in FIG. 16, specific coexisted gases such as nitrogen gas makes up most of the target gas 30. In this case, the influence of coexisted gases other than the specific coexisted gases to the absorption line is so small that the measurements of the quantities of state according to the present embodiment can be performed. This means that the measurements of the temperature and the pressure are possible with almost no influence by the concentration of the water vapor (namely, the target component) of the target gas 30. Therefore, even if the concentration of the water vapor is not known, the pressure and temperature of the target gas 30 can be determined using the relationship shown in FIG. 16. Here, the expression "the influence to the absorption line is so small that the measurements of the quantities of state according to the present embodiment can be performed" means that the extent of the influence of that coexisted gas is small. The extent of the influence can be evaluated by the partial pressures of the coexisted gases and the constants (above-described $\gamma i$) inherent to the coexisted gases.

In summary, in step S407, the peak-bottom ratio R calculated by the R calculating unit 42 and the temperature measured by the measurement apparatus 22 are inputted to the first determination unit 51. The first determination unit 51 determines the pressure of the target gas 30 from the peak-bottom ratio R by using the inputted temperature and the peak-bottom ratio R and referring to the data recorded in the memory unit 47, based on the predetermined relationship between the temperature, the pressure, and the peak-bottom ratio R. After step S407 being performed, according to the above-described flow 200, the concentration of the target gas 30 is measured.

Figure 17:
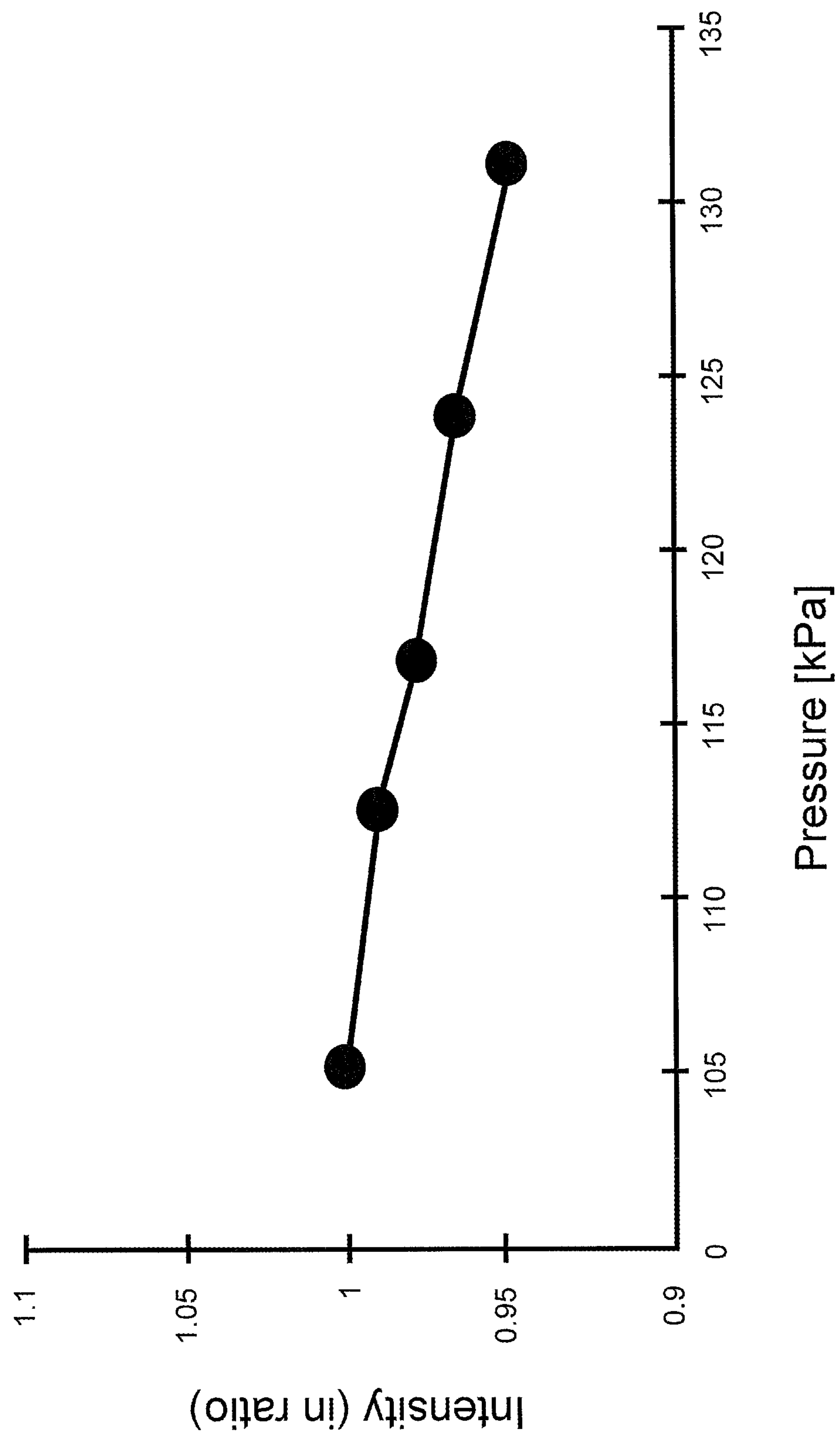
FIG. 17 is a graph that shows a relationship between a pressure and an intensity (in ratio) of a second harmonic component in a case of vapor water (width of wavelength modulation: 015 nm).

The intensity of the second harmonic component, namely P+N value, depends on the pressure and temperature of the target gas 30. FIG. 17 shows the result of the measured second harmonic component of the water vapor, which is the target component, with the pressure being varied, under the condition where the temperature of the target gas 30, the composition ratio of coexisted gases, and the width of wavelength modulation are constant. The result shown in FIG. 17 corresponds to that shown in FIG. 15(A). In FIG. 17, the intensity of the second harmonic component is shown as a relative number where the intensity at the pressure of 105 kPa is set unity. As shown in FIG. 17, the intensity of the second harmonic component of the water vapor decreases as the pressure increases. While the half-width of the absorption line is broadened as the pressure increases, the constant width of the wavelength modulation mainly causes the intensity to decrease as the pressure increases. Although it is only shown here by using the example that the intensity of the second harmonic component depends on the pressure, the intensity of the second harmonic component generally depends not only on pressures but also on temperatures.

Therefore, in order to measure the concentration of the target component using the intensity of the second harmonic component, the intensity of the second harmonic component may be calibrated in accordance with the pressure and the temperature. Information required for the calibration is obtained in advance and recorded in the memory unit 47 as data for the target component.

In step S408, the concentration measurement unit 46 refers to the data recorded in the memory unit 47 and calibrates the P+N value of the second harmonic component in accordance with the pressure and the temperature. Then, the concentration measurement unit 46 determines the concentration of the target component (the water vapor in the present embodiment), based on the calibrated P+N value of the second harmonic signal.

4.2 Effect of the Fourth Embodiment (1) In the gas measurement apparatus 1 according to the fourth embodiment, the first determination unit 51 determines the pressure referring to the peak-bottom ratio R that is the ratio of the magnitudes of the local minimum and the local maximum of the second harmonic component. Thus, the accuracy of the pressure measurement can easily be improved. In addition, the pressure is determined based on the predetermined relationship between the pressure and the peak-bottom ratio R, without any specific measuring instruments. Thus, since apparatuses to measure the pressure can be omitted, the measurement of the pressure can be simplified. As the result, the cost can be reduced.

(2) The gas measurement apparatus 1 further comprises the measurement apparatus 22 configured to measure the temperature that determines the state of the target gas 30. In addition, the first determination unit 51 determines the pressure using the peak-bottom ratio R and the measured temperature. Thus, according to the gas measurement apparatus 1, in the case where a plurality of quantities of state are measured, the number of measuring instruments to be used can be reduced.

(3) Since the predetermined relationship between the pressure and the peak-bottom ratio R is the relationship satisfied by the pressure and the peak-bottom ratio R when the target gas 30 is replaced by the standard sample, the calibration gas can be used as the standard sample. Thus, the relationship between the pressure and the peak-bottom ratio R can be determined in advance without preparing for special samples.

5. Other Embodiments

The embodiments described above are not limited to the above-described embodiments and can be modified in various ways without departing from the scope of the invention. Especially, the above-described embodiments can be combined with each other as appropriate.

(A) In the above-described embodiments, the standard gas used was the gas in which the pressure, the temperature, and the concentration were adjusted to predetermined values. However, kinds or states of the standard sample are not limited as long as the peak-bottom ratio R with which a desired width of wavelength modulation can be obtained can be determined. For example, the standard sample may be a gas with components that are not included in the target gas 30. The standard sample may also be a filter made of solid substances with absorption spectra. It is preferable that the quantities of state such as the pressure, temperature, and concentration of the component of the standard sample are well controlled.

However, the adjustment of the width of wavelength modulation is still possible even if the quantities of state of the standard sample are out of desired values, as long as there is the information to correct the influence caused by this deviation.

(B) In the above-described embodiments, the second harmonic component was obtained using WMS. However, the harmonic component obtained from the detection signal I1 may be the first harmonic component oscillated at the modulation frequency ω1 or the third or higher harmonic components. When the degree of the harmonic component is not two, the number of local minima and local maxima in the obtained absorption line is different from that of the second harmonic component. In this case, the setting of the modulation current can be performed by choosing any two or more of these local minima and local maxima and using the ratios between the chosen local minima and local maxima as an index quantity. In addition, in the above-described embodiments, the peak-bottom ratio R was calculated using one of two local minima. However, an average of the two local minima may be used in calculating the peak-bottom ratio R.

(C) In the above-described embodiments, the peak-bottom ratio R is used as an index quantity to characterize the second harmonic component and to correspond to the width of wavelength modulation. Quantities other than the peak-bottom ratio R may also be used as the index quantity. In setting the width of wavelength modulation, the index quantities may not be used.

For example, an embodiment described below can be performed using an apparatus, a method, or a program. In the embodiment described here, the recorder 41 records the central wavelength of the laser light and the value of the second harmonic component, with these values being associated with each other. To the recorder 41, the main current signal that is outputted from the wave mixer 12 and represents the main current, and the second harmonic signal I3 outputted from the first phase-sensitive detection apparatus 18, are inputted. The recorder 41 determines the values of the central wavelength and the second harmonic component based on the main current signal and the second harmonic signal I3, respectively. Then, the recorder 41 records the values of the central wavelength and the second harmonic component as X and Y values, respectively. The recorder 41 also records the value of the central wavelength of the laser light and the direct-current component of the detection signal I1, with these values being associated with each other.

In the present embodiment, in the above-described step S101, the main signal outputted from the wave mixer 12 is inputted to the recorder 41 of the computer 40. The main current signal is converted to the central wavelength and is recorded by the recorder 41. In the above-described step S103, the recorder 41 also records the second harmonic component associated with the central wavelength. The sweep performed in steps S101 to S104 enables a graph of the central wavelength as an X value and the second harmonic component as a Y value to be drawn. FIGS. 4(A) and (B) show the graphs of the central wavelengths as X values and the second harmonic components of water vapor as Y values. These graphs show the relationships between the central wavelength and the second harmonic component. In the present embodiment, the index quantity that characterizes the second harmonic component and is used to set the width of wavelength modulation may not be the peak-bottom ratio R. For example, the index quantity may be the quantity that can be determined by using the area on the X-Y graph of the central wavelength as the X value and the harmonic component as the Y value. Specifically, an integral of the X-Y graph can be used. More specifically, the index quantity may be a ratio AP/AN, where AN is an integral of the graph in the region including the local minimum and AP is an integral of the graph in the region including the local maximum (refer to FIG. 5).

An extent of the agreement of a standard X-Y graph and the X-Y graph obtained in setting the width of wavelength modulation may also be determined. For example, the X-Y graph obtained using the desired width of wavelength modulation may be chosen as the standard X-Y graph and recorded in the memory unit 47 in advance as the combination of the X and Y values. Then, these X and Y values may be compared with those of the graph obtained in setting the width of wavelength modulation. In this case, it is the condition to end the setting of the width of wavelength modulation that the extent of the agreement of the X-Y graphs is higher than a predetermined threshold (an example of a predetermined condition). In calculating the extent of the agreement, since there are a plurality of combinations of the X and Y values, a multivariate analysis can be used for the comparison.

It should be noted that, in the present embodiment, the central wavelength was obtained from the main current signal. However, as described above, the relationship between the driving current inputted to the light source 2 and the wavelength of the oscillated laser light depends on the properties of semiconductor laser devices. The central wavelength obtained in the present embodiment is an estimate obtained based on the main current. Namely, the value of the central wavelength does not have to be specified accurately and the X value may not be the value of the central wavelength. The X value may be a value that represents the magnitude of a main input inputted to the light source 2. Here, the main input is a signal that is inputted to the light source 2 and has a magnitude almost constant during one period of the modulation current. The above-described main current signal can be an example of the main input. Therefore, the intensity of the main current can be used as the X value of the X-Y graph.

In addition, if the rate of the increase of the ramp current to time is known, the intensity of the main current can be estimated from the time elapsed from the start of the sweep. Namely, if a timing when the first phase-sensitive detection apparatus 18 obtains the second harmonic component is known, the intensity of the main current can be estimated without the main current signal. For this, time can be used as the X value of the X-Y graph. For example, the first phase-sensitive detection apparatus 18 and the recorder 41 may be controlled such that the derivation of the second harmonic component by the first phase-sensitive detection apparatus 18 is performed at a constant interval. Thus, time can be the X value of the X-Y graph. The X value corresponds to the main current signal as the main input while the X value is time.

In summary, the gas measurement apparatus according to the present embodiments can be described as follows. The gas measurement apparatus measures the target gas. The gas measurement apparatus comprises the light source, the detection unit, the obtaining unit, and the setting unit. The light source oscillates the laser light that has the central wavelength determined by the main current and is modulated according to the modulation current, with the central wavelength being varied. The detection unit outputs the detection signal according to the intensity of the laser light transmitted through the standard sample. The obtaining unit obtains, from the detection signal, the specific frequency component oscillated at the frequency that is a positive integral multiple of the oscillation frequency of the modulation signal. The setting unit sets the width of wavelength modulation of the laser light so that the relationship between the main input and the specific frequency component meets the predetermined condition.

Here, the modulation current is an example of 'the modulation signal' in the above description. The X-Y graph of the second harmonic component is an example of 'the relationship between the main input and the specific frequency component' in the above expression. The expression 'the relationship between the main input and the specific frequency component satisfies the predetermined condition' means that the peak-bottom ratio R equals to the target value in the above-described embodiments. As described in the present embodiment, it is one example of 'the predetermined condition' that the ratio AP/AN equals to the predetermined value. It is another example of 'the predetermined condition' that the extent of the agreement of the shapes of the X-Y graphs is higher than the predetermined threshold.

(D) In the above-described first embodiment, the gas measurement apparatus 1 automatically changes the intensity of the modulation current so that the peak-bottom ratio R equals to the target value. However, the adjustment of the modulation current can be performed manually. For example, a numerical value that represents the deviation of the peak-bottom ratio R from the target value is displayed on the display 60. Then, the operator changes the modulation current with the input device 70 such that the numerical value becomes zero, while checking the numerical value displayed on the display 60.

In addition, in the above-described third embodiment, the computer 40 determined whether the time during which the measurements have continued was beyond the predetermined time or not, and then the setting of the width of wavelength modulation started automatically. Namely, the width of wavelength modulation was calibrated automatically. However, the setting of the width of wavelength modulation may not start automatically. For example, the operator can decide whether the adjustment of the modulation current is required or not. In this case, the operator gives a direction to the gas measurement apparatus 3 with the input device 70. When the direction is inputted, the gas measurement apparatus 3 performs the setting of the modulation current.

(E) In the above-mentioned first embodiment, the setting of the width of wavelength modulation was performed as the initial adjustment of the gas measurement apparatus 1. However, the setting of the width of wavelength modulation is not limited to be performed as the initial adjustment. The setting of the width of wavelength modulation may be performed after stopping the measurement of the target gas 30 and then replacing the target gas 30 to the standard sample.

In the above-described third embodiment, the continuation time was compared with the period of the regular maintenance. However, the standard for the comparison of the continuation time of the measurements can be determined on a voluntary basis. Namely, any periods can be used as the standard for the comparison of the continuation time as long as the width of wavelength modulation can be kept to have the appropriate value.

(F) In the above-described embodiments, in measuring the concentration of the target component, the sweep was performed by the ramp current. However, WMS can also be performed without using the sweep by the ramp current.

(G) In the above-described embodiments, the width of wavelength modulation was determined by taking the fluctuation rate of the second harmonic component to the fluctuation of the pressure and the S/N ratio into consideration. However, the width of wavelength modulation may be determined by taking factors other than these two factors into account. For example, the width of wavelength modulation may be determined based on a resolution of the gas measurement apparatus 1. When the width of wavelength modulation is large, the absorption of the laser light into components other than the target component may cause the deviation of the measurement. Therefore, the magnitude of the width of wavelength modulation may be limited in order to prevent the resolution from being lowered. Thus, the width of wavelength modulation can be determined by taking the fluctuation of the second harmonic component to the fluctuation of the pressure, the S/N ratio, and the resolution, into consideration. However, not all of these factors have to be taken into account. The width of wavelength modulation may be determined by taking only one or two of these factors into account.

Therefore, a target width of wavelength modulation may be determined without taking the fluctuation rate of the second harmonic component to the fluctuation of the pressure into account. In this case, the pressure of the target gas 30 may be measured and then the intensity of the second harmonic component may be calibrated based on the pressure.

(H) The above-described setting of the width of wavelength modulation and measurement of the concentration may be performed on site where the target gas 30 exists. The setting and measurement may also be performed off-site by sampling the target gas 30. According to the method of setting the width of wavelength modulation disclosed here, since a wavelength measurement apparatus is not required, the setting of the width of wavelength modulation can be performed off the site, into which it is difficult to bring the wavelength measurement apparatus.

(I) In the above-described fourth embodiment, the temperature was measured by the measurement apparatus 22 and the pressure was measured by the first determination unit 51. However, the measurement apparatus 22 can measure quantities of state other than temperature and the first determination unit 51 can measure quantities of state other than the pressure. For example, the measurement apparatus 22 may measure the pressure (an example of a measurable quantity of state) and the first determination unit 51 may measure the temperature (an example of a quantity of state). In this case, the peak-bottom ratio R calculated by R calculating unit 42 and the pressure measured by the measurement apparatus 22 are inputted to the first determination unit 51. The first determination unit 51 determines the temperature referring to the peak-bottom ratio R, based on the predetermined relationship between the temperature and the peak-bottom ratio R. More specifically, the first determination unit 51 determines the temperature of the target gas 30 based on the predetermined relationship between the peak-bottom ratio R, the temperature, and the pressure, by using the inputted pressure and peak-bottom ratio R and referring to the data recorded in the memory unit 47. Like the above-described embodiment, the data shown in FIG. 6 is recorded in the memory unit 47 and used as the predetermined relationship.

The first determination unit 51 may also measure the partial pressure of the coexisted gas (an example of a quantity of state) included in the target gas 30. In this case, all quantities of state other than the partial pressure of the target component (an example of a measurable quantity of state) are measured by the measurement apparatus 22 or other means. In advance, the standard sample is prepared and the peak-bottom ratio R is measured, with the pressure, temperature, and partial pressures of the standard sample being varied. Here, the coexisted gases included in the standard sample are the same as the coexisted gases that are included in the target gas 30 and possibly influence the absorption line of the target component. Information of the pre-measured peak-bottom ratio R is recorded in the memory unit 47 such that the information is associated with the temperature, the pressure, and the partial pressures of the coexisted gases (an example of a group of quantities of state). In measuring the partial pressures of the coexisted gases, the first determination unit 51 determines the partial pressure of the specific coexisted gas by using the quantities of state measured by the measurement apparatus 22 or other means and the peak-bottom ratio R calculated by the R calculating unit 42, and by referring to the data recorded in the memory unit 47.

Thus, by using the method disclosed here, the partial pressures of the coexisted gases that can influence the absorption line of the target component can be measured. Furthermore, the quantities of state other than the pressure, the temperature, and the partial pressures of the coexisted gases that can influence the absorption line of the target component may be measured using the method disclosed here.

(J) In the above-described fourth embodiment, the relationship between the pressure, the temperature, and the peak-bottom ratio R was expressed as numerical data. However, this relationship may be expressed as formulae. For example, a formula that expresses the pressure as a function of two variables of the peak-bottom ratio R and the temperature may be prepared in advance. In this case, the first determination unit 51 calculates the pressure by substituting the temperature measured by the measurement apparatus 22 and the peak-bottom ratio R calculated by the R calculating unit 42 into this function.

(K) In the above-described fourth embodiment, the width of wavelength modulation used for the determination of the quantities of state of the target gas 30 (namely, in steps S401 to S404 shown in FIG. 13) may be different from that used for the measurement of the concentration. Namely, each second harmonic component described above may be obtained by using the width of wavelength modulation suitable for the determination of quantities of state or the measurement of the concentration of the target component. Thus, both the quantities of state of the target gas 30 and the concentration of the target component can be measured accurately.

(L) In the above-described fourth embodiment, the computer 40 included the comparing unit 43 configured to compare the peak-bottom ratio R with the target value and the setting unit 44 configured to output the control signal S4 for varying the intensity of the modulation current when the peak-bottom ratio R is different from the target value. In addition, in the above-described fourth embodiment, the concentration measurement flow 200 included the flow 100 for adjusting the width of wavelength modulation in FIG. 13 showing the flowchart for determining the pressure of the target gas 30. However, the embodiment described here is not limited to these. The computer 40 may not include the comparing unit 43 and the setting unit 44. In the flowchart showing the determination of the pressure of the target gas, the flow 100 for adjusting the width of wavelength modulation may be omitted. Such embodiment can be used in the situation for example where the setting of the width of the wavelength modulation is not necessary (for example, when the width of wavelength modulation suitable for the measurement of the concentration of the target component is known in advance.). Thus, the time for measuring the quantities of state of the target gas 30 and the concentration of the target component can be reduced.

(M) The processes in the above-described embodiments may be realized in hardware or software (including the case where the processes are realized in operating system, middleware, or predetermined libraries). These processes may be a mixture of processes realized in hardware and those realized in software. The executing orders of the processes in the above-described embodiments is not necessarily limited to the orders described in the above-described embodiments and may be changed without departing from the scope of the invention. The programs for performing the processes in the above-described embodiment can be recorded in the memory unit 47 or on the removable recording media 50.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A gas measurement apparatus for measuring a target gas, comprising:

- a light source configured to oscillate a laser light that has a central wavelength determined by a main current and is modulated according to a modulation current, while varying the central wavelength;
- a detection unit configured to output a detection signal according to an intensity of the laser light transmitted through a standard sample;
- an obtaining unit configured to obtain a specific frequency component of the detection signal that is oscillated at a frequency that is a positive integral multiple of an oscillation frequency of the modulation current;
- a calculation unit configured to calculate a ratio of a magnitude of a local minimum of the specific frequency component and a magnitude of a local maximum of the specific frequency component; and
- a setting unit configured to set a width of a wavelength modulation of the laser light so that the ratio satisfies a predetermined condition.

2. The gas measurement apparatus according to claim 1, wherein the predetermined condition is a condition where the ratio that corresponds to the width of the wavelength modulation in one-to-one equals to a predetermined target value; and the setting unit sets the width of the wavelength modulation by adjusting an intensity of the modulation current.

3. The gas measurement apparatus according to claim 2, wherein the target value is determined based on a fluctuation rate of the specific frequency component in a case where a pressure of the standard sample is varied.

4. The gas measurement apparatus according to claim 1, further comprising:

- a counting unit configured to count a continuation time during which measurements of the target gas have been performed; and
- wherein the setting unit sets the width of the wavelength modulation so that the ratio satisfies the predetermined condition when the continuation time is beyond a predetermined time.

5. The gas measurement apparatus according to claim 1, further comprising:

- a determination unit configured to determine quantities of state using the ratio, based on a predetermined relationship between the ratio and the quantities of state that determine a state of the target gas.

6. The gas measurement apparatus according to claim 5, further comprising:

- a measurement unit configured to measure one or a plurality of measurable quantities of state that determine the state of the target gas; and
- wherein the determination unit determines the quantities of state by using the ratio and measured one or plurality of the measurable quantities of state.

7. The gas measurement apparatus according to claim 5, wherein the predetermined relationship between the quantities of state and the ratio is a relationship satisfied by the quantities of state and the ratio when the target gas is replaced by the standard gas.

8. The gas measurement apparatus according to claim 5, wherein the quantity of state determined by the determination unit is a temperature of the target gas.

9. The gas measurement apparatus according to claim 5, wherein the quantity of state determined by the determination unit is a pressure of the target gas.

10. The gas measurement apparatus according to claim 6, wherein the predetermined relationship between the quantities of state and the ratio is a relationship satisfied by the ratio and a group of quantities of state that includes one or a plurality of the measurable quantities of state and the quantities of state determined by the determination unit and determines the states of the target gas.

11. The gas measurement apparatus according to claim 10, wherein the group of quantities of state includes a temperature and a pressure of the target gas.

12. A method of setting a width of wavelength modulation of a gas measurement apparatus comprising a light source configured to oscillate a laser light that has a central wavelength determined by a main current and is modulated according to a modulation current and a detection unit configured to output a signal according to an intensity of the laser light transmitted through a target gas, comprising:

obtaining a detection signal by detecting the laser light transmitted through the standard sample, while varying the central wavelength;

obtaining a specific frequency component of the detection signal that is oscillated at a frequency that is a positive integral multiple of an oscillation frequency of the modulation current;

calculating a ratio of a magnitude of a local minimum of the specific frequency component and a magnitude of a local maximum of the specific frequency component; and setting the width of the wavelength modulation of the laser light so that the ratio satisfies a predetermined condition.

13. The method of setting the width of wavelength modulation according to claim 12, wherein the predetermined condition is a condition where the ratio that corresponds to the width of the wavelength modulation in one-to-one equals to a predetermined target value; and, in setting the modulation width of the laser light, the width of the wavelength modulation is set by adjusting an intensity of the modulation current.

14. The method of setting the width of wavelength modulation according to claim 13, wherein the target value is determined based on a fluctuation rate of the specific frequency component in a case where a pressure of the standard sample is varied.

15. The method of setting the width of the wavelength modulation according to claim 12, further comprising:

counting a continuation time during which measurements of the target gas have been performed; and wherein the width of the wavelength modulation is set so that the ratio satisfies the predetermined condition when the continuation time is beyond a predetermined time.

16. The method of setting the width of wavelength modulation according to claim 12, further comprising:

determining quantities of state using the ratio, based on a predetermined relationship between the quantities of state that determine a state of the target gas and the ratio.

17. The method of setting the width of wavelength modulation according to claim 16, further comprising:

measuring one or a plurality of measurable quantities of state that determine the state of the target gas; and wherein, in determining the quantities of state, the quantities of state are determined from the ratio and measured one or plurality of the measurable quantities of state.

18. The method of setting the width of the wavelength modulation according to claim 16, wherein the predetermined relationship between the quantities of state and the ratio is a relationship satisfied by the quantities of state and the ratio when the target gas is replaced by the standard sample.

19. The method of setting the width of the wavelength modulation according to claim 17, wherein the predetermined relationship between the quantities of state and the ratio is a relationship satisfied by the ratio and a group of quantities of state that includes one or a plurality of the measurable quantities of state and the quantities of state determined in determining the quantities of state and determines the state of the target gas.

20. A non-transitory storage medium storing a program that causes a computer to perform a method of setting a width of wavelength modulation used by a gas measurement apparatus comprising a light source configured to oscillate a laser light that has a central wavelength determined by a main current and is modulated according to a modulation current while varying the central wavelength, a detection unit configured to output a detection signal according to an intensity of the laser light transmitted through a standard sample, and an obtaining unit configured to obtain a specific frequency component of the detection signal that is oscillated at a frequency that is a positive integral multiple of a oscillation frequency of the modulation current, comprising:

calculating a ratio of a magnitude of a local minimum of the specific frequency component and a magnitude of local maximum of the specific frequency component; and setting a width of the wavelength modulation of the laser light so that the ratio satisfies a predetermined condition.

* * * * *

UNITED STATES PATENT AND TRADEMARK OFFICE

CERTIFICATE OF CORRECTION

PATENT NO. : 8,896,835 B2
APPLICATION NO. : 13/723367
DATED : November 25, 2014
INVENTOR(S) : Takuya Ido et al.

It is certified that error appears in the above-identified patent and that said Letters Patent is hereby corrected as shown below:

In the claims,

Column 28, Line 46, Claims 20:

After “integral multiple of”
Delete “a” and insert -- an --.

Signed and Sealed this
Twenty-first Day of July, 2015

Michelle K. Lee

Michelle K. Lee
*Director of the United States Patent and Trademark Office*